United States Patent
Cheng

(10) Patent No.: US 9,433,635 B2
(45) Date of Patent: *Sep. 6, 2016

(54) EFFECTIVE TREATMENT OF OVARIAN CANCER USING TRICIRIBINE AND RELATED COMPOUNDS

(71) Applicant: University of South Florida, Tampa, FL (US)

(72) Inventor: Jin Q. Cheng, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/534,705

(22) Filed: Nov. 6, 2014

(65) Prior Publication Data

US 2015/0209378 A1    Jul. 30, 2015

Related U.S. Application Data

(63) Continuation of application No. 13/936,864, filed on Jul. 8, 2013, now Pat. No. 8,906,869, which is a continuation of application No. 12/206,504, filed on Sep. 8, 2008, now abandoned.

(60) Provisional application No. 60/935,942, filed on Sep. 7, 2007.

(51) Int. Cl.
| | | |
|---|---|---|
| *A61K 31/70* | (2006.01) | |
| *A61K 31/7052* | (2006.01) | |
| *A61K 31/7056* | (2006.01) | |
| *A61K 31/706* | (2006.01) | |
| *C07H 19/04* | (2006.01) | |
| *G01N 33/574* | (2006.01) | |

(52) U.S. Cl.
CPC .......... *A61K 31/7056* (2013.01); *A61K 31/706* (2013.01); *C07H 19/04* (2013.01); *G01N 33/57449* (2013.01)

(58) Field of Classification Search
CPC ...................... A61K 31/7064; A61K 31/7052; A61K 31/7042; A61K 31/706; A61K 31/7056; A61K 31/0019; A61K 9/127; A61K 9/14; A61K 9/20; C07H 19/04; C07H 19/23
USPC ............... 514/43, 52, 42, 23; 536/27.1, 22.1
See application file for complete search history.

(56) References Cited

PUBLICATIONS

Notice of Allowance in U.S. Appl. No. 13/936,864, now U.S. Pat. No. 8,906,869, mailed Aug. 6, 2014.
Non-Final Office Action in U.S. Appl. No. 13/936,864, now U.S. Pat. No. 8,906,869, mailed Apr. 1, 2014.
Schilcher, et al.; Journal of Chromatography, vol. 337(1), pp. 55-62, 1985.

*Primary Examiner* — Shaojia Anna Jiang
*Assistant Examiner* — Michael C Henry
(74) *Attorney, Agent, or Firm* — Fanelli Haag PLLC

(57) ABSTRACT

The inventors have determined, contrary to the prior art and experience, how to successfully use triciribine to treat ovarian cancer by one or a combination of (i) administering triciribine only to patients which according to a diagnostic test described below, exhibit enhanced sensitivity to the drug; (ii) use of a described dosage level that minimizes the toxicity of the drug but yet still exhibits efficacy; or (iii) use of a described dosage regimen that minimizes the toxicity of the drug.

7 Claims, 8 Drawing Sheets

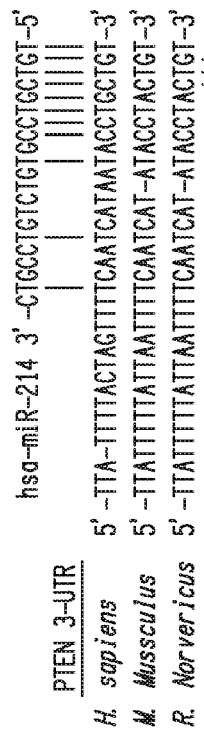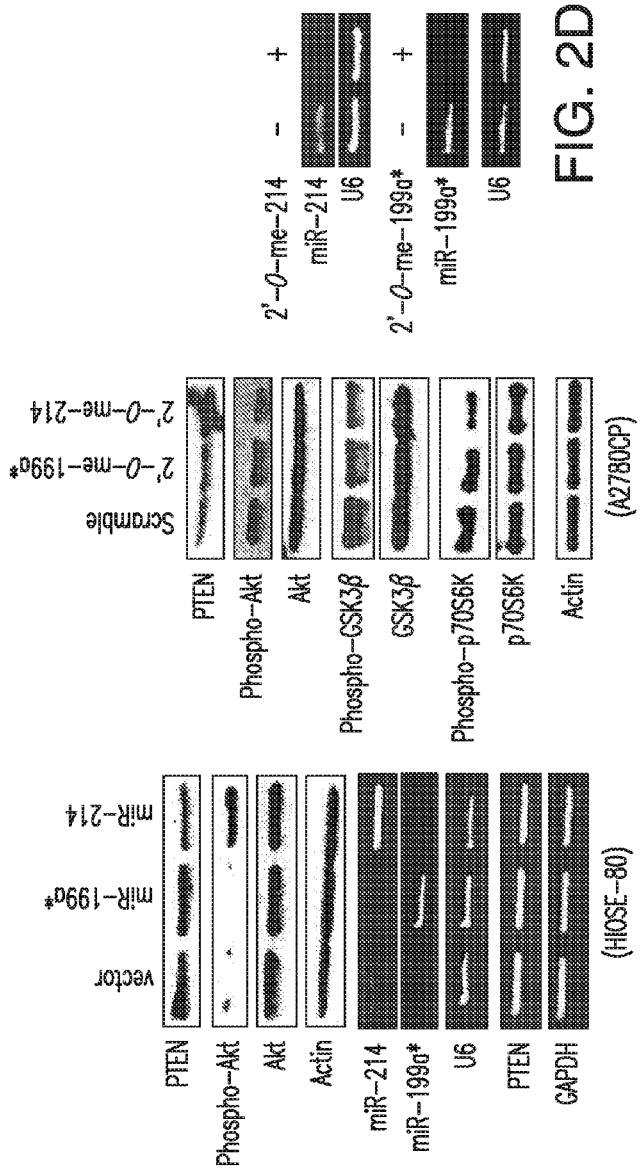

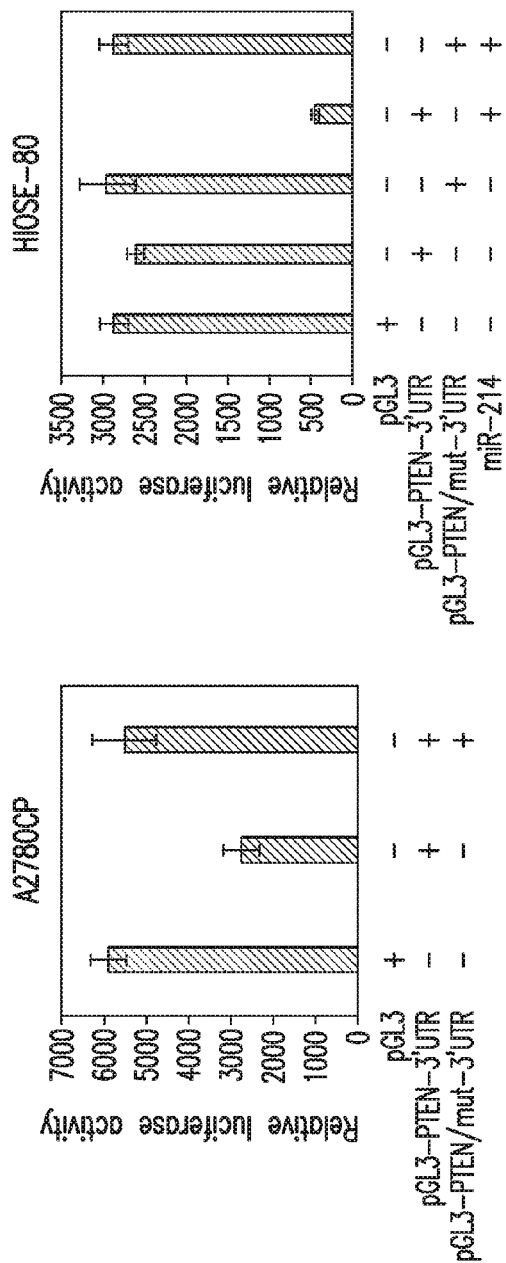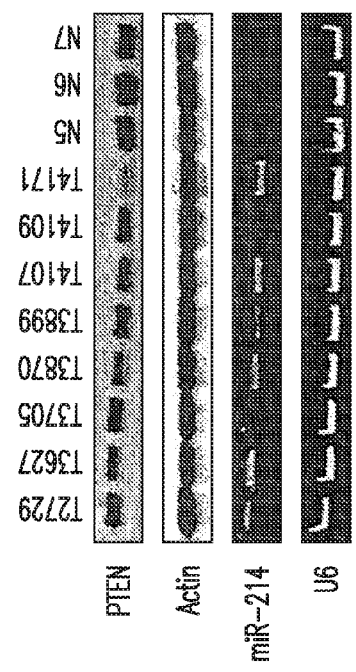
FIG. 2E
FIG. 2F

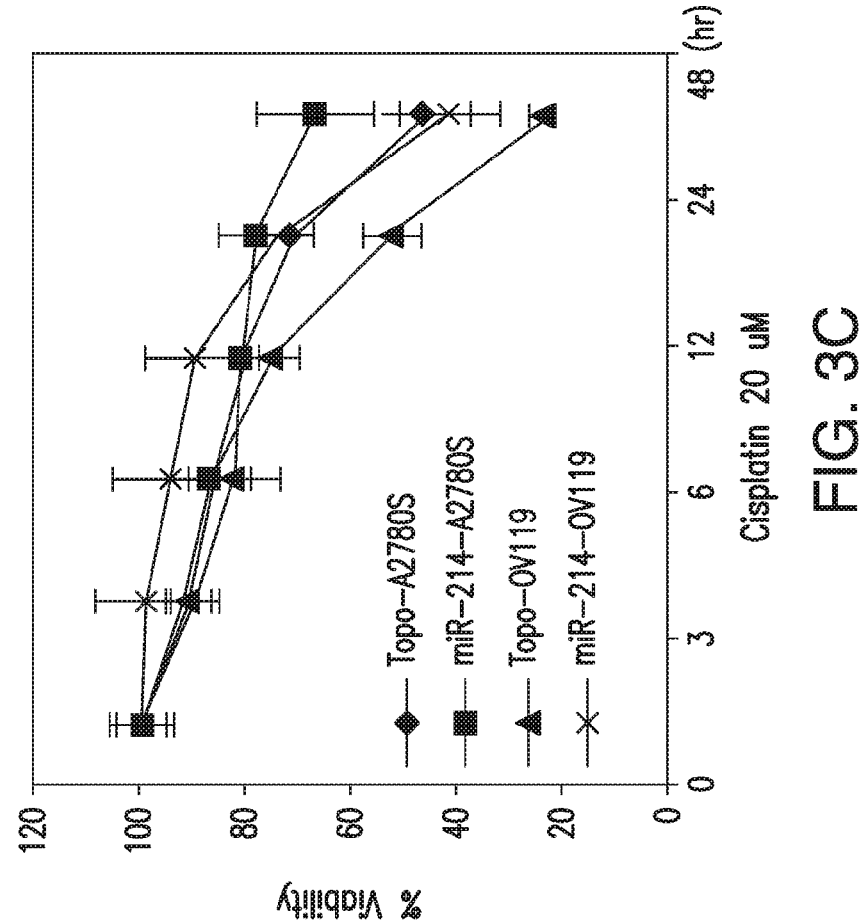
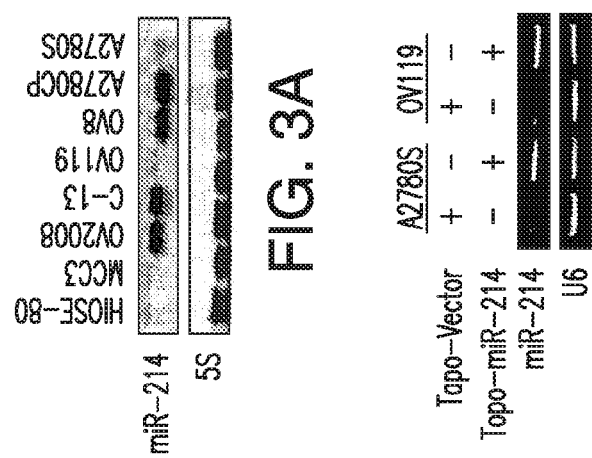
FIG. 3A
FIG. 3B
FIG. 3C

EFFECTIVE TREATMENT OF OVARIAN CANCER USING TRICIRIBINE AND RELATED COMPOUNDS

CROSS-REFERENCE TO RELATED APPLICATIONS

This application is a continuation of U.S. application Ser. No. 13/936,864, which is allowed, which is a continuation of U.S. application Ser. No. 12/206,504, which was filed Sep. 8, 2008, and is abandoned, and claims the benefit of U.S. provisional patent application No. 60/935,942, which was filed Sep. 7, 2007, the disclosures of each of which is incorporated herein by reference in their entireties.

Sequence Listing A computer readable text file, entitled "1018895004US1SequenceListing.txt," created on or about Jun. 1, 2009 having a size of about 4 kb contains the sequence listing for this application and is hereby incorporated by reference.

STATEMENT REGARDING FEDERALLY SPONSORED RESEARCH

This application may claim subject matter that was developed using grants from the National Institute of Health and the Department of Defense.

TECHNICAL FIELD

This application provides particular therapeutic regimens of triciribine and related compounds and compositions with reduced toxicity for the treatment of ovarian cancer and other disorders associated with abnormal cell proliferation.

BACKGROUND

MicroRNAs (miRNAs) are a class of 22-nt noncoding RNAs, which are evolutionarily conserved and function as negative regulators of gene expression. Like conventional protein-coding mRNA, miRNAs are transcribed by RNA polymerase II, spliced and polyadenylated (called primitive miRNA or pri-miRNA). However, unlike mRNA, the pri-miRNAs contain a stem-loop structure that can be recognized and excised by the RNAi machinery to generate hairpin precursor miRNAs (pre-miRNA) that are ~70 nt in animals or ~100 nt in plants. Pre-miRNAs are cleaved by cytoplasmic RNase III Dicer into a ~22-nucleotide miRNA duplex: one strand (miRNA *) of the short-lived duplex is degraded, whereas the other strand serves as a mature miRNA. The mature miRNA then guides a complex called miRNP (miRNA-containing ribonucleo-protein particles) to the complementary site(s) in the 3' untranslated region (UTR) of a target mRNA. Consequently, translation blockade or mRNA degradation will occur depending on whether it is partially matched or completely matched with the target genes, respectively (1). Moreover, the levels of individual miRNAs are dramatically changed in different cell types and different developmental stages, suggesting that miRNA plays a role in cell growth, differentiation, and programmed cell death (1, 2). miRNAs have been shown to be aberrantly expressed or mutated in human cancer, indicating that they may function as a novel class of oncogenes or tumor suppressor genes (3-9). The first evidence of involvement of miRNAs in human cancer came from molecular studies characterizing the 13q 14 deletion in human chronic lymphocytic leukemia, which revealed two miRNAs, miR-15a and miR-16-1 (3). Subsequently, miRNA deregulation was detected in other human malignancies, including breast carcinoma (4, 5), primary glioblastoma (6, 7), lung cancer (8), papillary thyroid carcinoma (9), colon carcinoma (10) and pancreatic tumors (11, 12). For instance, the miR-17-92 cluster is upregulated in B-celllymphomas and lung cancer. miR-143 and -145 are down-regulated in colon carcinomas. A decrease in Let-7 is detected in human lung carcinomas and restoration of its expression induces cell growth inhibition in lung cancer cells (13). The BIC gene, which contains the miR-155, is up-regulated in some Burkitt's lymphomas and several other types of lymphomas (14, 15).

SUMMARY OF THE INVENTION

The invention is based on the discovery that deregulation was shown in a number of miRNAs in human ovarian cancer. The aberrant expression of miR-214, -199a*, -200a and -100 was detected in a near or over half of ovarian cancers, especially in late stage and high grade tumors. Significantly, we demonstrated that miR-214 negatively regulates PTEN by binding to its 3-'UTR leading to inhibition of PTEN translation and activation of Akt pathway. As a result, miR-214 induces cell survival and cisplatin resistance, which were overridden by either small molecule Akt inhibitor or expression of PTEN cDNA lacking 3-'UTR.

The invention is based on the discovery that ovarian cancer, which overexpress Akt kinase are particularly sensitive to the cytotoxic effects of TCN and related compounds. The inventors have determined, contrary to the prior art and experience, how to successfully use triciribine to treat ovarian cancer by one or a combination of (i) administering triciribine only to patients which according to a diagnostic test described below, exhibit enhanced sensitivity to the drug; (ii) use of a described dosage level that minimizes the toxicity of the drug but yet still exhibits efficacy; or (iii) use of a described dosage regimen that minimizes the toxicity of the drug.

In one aspect of the present invention, methods are provided to identify ovarian cancer susceptible to the toxic effects of TCN, TCN-P and/or related compounds. In one embodiment, methods are provided for treating ovarian cancer in a mammal, particularly a human that includes (i) obtaining a biological sample from the tumor; (ii) determining whether the tumor overexpresses an Akt kinase, and (iii) treating the tumor that overexpresses Akt kinase with triciribine, triciribine phosphate or a related compound as described herein. In one embodiment, the level of Akt kinase expression can be determined by assaying the ovarian cancer cells for the presence of a phosphorylated Akt kinase, for example, by using an antibody that can detect the phosphorylated form. In another embodiment, the level of Akt expression can be determined by assaying a ovarian cancer cell obtained from a subject and comparing the levels to a control tissue. In certain embodiments, the Akt can be overexpressed at least 2, 2.5, 3 or 5 fold in the ovarian cancer sample compared to the control. In certain embodiments, the overexpressed Akt kinase can be a hyperactivated and phosphorylated Akt kinase.

In another aspect of the present invention, dosing regimens are provided that limit the toxic side effects of TCN and related compounds. In one embodiment, such dosing regimens minimize or eliminate toxic side effects, including, but not limited to, hepatoxicity, thrombocytopenia, hyperglycemia, vomiting, hypocalcemia, anemia, hypoalbunemia, myelosuppression, hypertriglyceridemia, hyperamylasemia, diarrhea, stomatitis and/or fever. In another embodiment, the administration of TCN, TCN-P or related compounds provides at least a partial, such as at least 15, 20 or 30%, or complete response in vivo in at least 15, 20, or 25% of the subjects.

In one embodiment, a method is provided to treat a subject which has been diagnosed with ovarian cancer by administering to the subject an effective amount of TCN, TCN-P or a related compound, for example compounds described herein, according to a dosing schedule that includes administering the drug approximately one time per week for approximately three weeks followed by a one week period wherein the drug is not administered. In another embodiment, methods are provided to treat ovarian cancer in a subject by administering to the subject a dosing regimen of 10 mg/m$^2$ or less of TCN, TCN-P or a related compound one time per week. In one embodiment, the compound can be administered as a single bolus dose over a short period of time, for example, about 5, 10 or 15 minutes. In further embodiments, dosing schedules are provided in which the compounds are administered via continuous infusion for at least 24, 48, 72, 96, or 120 hours. In certain embodiments, the continuous administration can be repeated at least once a week, once every two weeks and/or once a month. In other embodiments, the compounds can be administered at least once every three weeks. In further embodiments, the compounds can be administered at least once a day for at least 2, 3, 4 or 5 days.

In further embodiments, TCN, TCN-P and related compounds as disclosed herein can be administered to patients in an amount that is effective in causing ovarian cancer regression. The administration of TCN, TCN-P or related compounds can provide at least a partial, such as at least 15, 20 or 30%, or complete response in vivo in at least 15-20% of the subjects. In certain embodiments, at least 2, 5, 10, 15, 20, 30 or 50 mg/m$^2$ of a compound disclosed herein can be administered to a subject. The administration of the compound can be conducted according to any of the therapeutic regimens disclosed herein.

In particular embodiments, the dosing regimen can include administering less than 20 mg/m$^2$ of TCN and related compounds. In one embodiment, less than 10 mg/m$^2$ of TCN or related compounds can be administered once a week. In further embodiments, dosages of or less than 2 mg/m$^2$, 5 mg/m$^2$, 10 mg/m$^2$, and/or 15 mg/m$^2$ of TCN or a related compound can be administered to a subject. In another embodiment, less than 10 mg/m$^2$ can be administered to a subject via continuous infusion for at least five days. In particular embodiments, TCN or a related compound as disclosed herein can be used for the treatment of ovarian cancer.

In one embodiment, the compounds and/or therapeutic regimens of the present invention can be used to prevent and/or treat ovarian cancer. In particular embodiments, TCN or a related compound as disclosed herein can be used for the treatment of ovarian cancer. In further embodiments of the present invention, the compounds disclosed herein can be used in the treatment of angiogenesis-related diseases. In certain embodiments, methods are provided to treat ovarian cancer via continuous infusion of TCN, TCN-P or a related compound via continuous infusion for at least 24, 48, 72 or 96 hours. In other embodiments, the continuous infusion can be repeated, for example, at least once every two, three or four weeks.

In a particular embodiment, there is provided a method for the treatment of ovarian cancer, and others disorders associated with an abnormal cell proliferation in a host, the method comprising administering to the host an effect amount of a compound disclosed herein optionally in combination with a pharmaceutically acceptable carrier.

In one aspect, the compounds and compositions can be administered in combination or alternation with at least one additional chemotherapeutic agent. The drugs can form part of the same composition, or be provided as a separate composition for administration at the same time or a different time. In one embodiment, compositions of the invention can be combined with antiangiogenic agents. In other embodiments of the present invention, the compounds and compositions disclosed herein can be used in combination or alternation with the following types of drugs, including, but not limited to: antiproliferative drugs, antimitotic agents, antimetabolite drugs, alkylating agents or nitrogen mustards, drugs which target topoisomerases, drugs which target signal transduction in tumor cells, gene therapy and antisense agents, antibody therapeutics, steroids, steroid analogues, anti-emetic drugs and/or nonsteroidal agents.

In other embodiments, TCN, TCN-P or a related compound as disclosed herein can be used to treat ovarian cancer resistant to one or more drugs, including the embodiments of ovarian cancer and drugs disclosed herein. In one embodiment, TCN, TCN-P or a related compound as disclosed herein is administered in an effective amount for the treatment of a patient with a drug resistant ovarian cancer, for example, multidrug resistant ovarian cancer, including but not limited to those resistant to taxol, rapamycin, tamoxifen, cisplatin, and/or gefitinib (iressa). In one embodiment, the TCN, TCN-P or related compound as disclosed herein can be administered with an additional chemotherapeutic agent that can be a P-glycoprotein inhibitor, such as verapamil, cyclosporin (such as cyclosporin A), tamoxifen, calmodulin antagonists, dexverapamil, dexniguldipine, valspodar (PSC 833), biricodar (VX-710), tariquidar (XR9576), zosuquidar (LY335979), laniquidar (R101933), and/or ONT-093.

In certain embodiments, a method is provided including administering to a host in need thereof an effective amount of a compound disclosed herein, or pharmaceutical composition comprising the compound, in an effective amount for the treatment of the treatment of tumors, cancer, and others disorders associated with an abnormal cell proliferation in a host.

In one embodiment, a method for the treatment of a ovarian cancer is provided including an effective amount of a compound disclosed herein, or a salt, isomer, prodrug or ester thereof, to an individual in need thereof. The compound, or salt, isomer, prodrug or ester thereof, is optionally provided in a pharmaceutically acceptable composition including the appropriate carriers, such as water, which is formulated for the desired route of administration to an individual in need thereof. Optionally the compound is administered in combination or alternation with at least one additional therapeutic agent for the treatment of ovarian cancer.

Also within the scope of the invention is the use of a compound disclosed herein or a salt, prodrug or ester thereof in the treatment of ovarian cancer, optionally in a pharmaceutically acceptable carrier; and the use of a compound disclosed herein or a salt, prodrug or ester thereof in the manufacture of a medicament for the treatment of cancer or tumor, optionally in a pharmaceutically acceptable carrier.

BRIEF DESCRIPTION OF THE DRAWINGS

FIG. 2A-FIG. 2F miR-214 negatively regulates PTEN through binding to 3'UTR of the PTEN. (A) Sequence alignment of human miR-214 with 3'UTR of PTEN. The seed sequence of miR-214 (upper) matches 3'UTR of PTEN (middle). Bottom panel shows mutations of the 3'UTR of PTEN for creating the mutant luciferaase reporter construct. (B) Ectopic expression of miR-214 decreases PTEN protein but not mRNA levels. HIOSE-80 cells were transfected with pcDNA3.1N5-His-Topo-miR-214, -miR199a* and vector alone and immunoblotted with indicated antibodies (panels 1-4). The expression of miR-214 and miR-199a* was determined by qRT-PCR (panels 5 and 6). PTEN mRNA level was measured by RT-PCR (panel 8). U6 (panel 7) and GAPDH (bottom panel) were used for controls. (C and D) Knockdown of miR-214 induces PTEN expression. A2780CP cells were transfected with antisense 2'-O-methyl oligonucleotide targeting miR-214 at concentration of 150 pM/well (6 well plate) with Lipofectamine 2000. Anti-miR199a* and scramble 2'-O-methyl oligonucleotide were used as controls. After incubation of 72 h, cells were lysed and immunoblotted with indicated antibodies (C). Inhibition of miR-199, 214 and miR-199a* expression by 2'-O-methyl oligonucleotide in A2780CP cells was demonstrated by qRT-PCR (D). (E) miR-214 inhibits wild-type but not mutated PTEN-3'UTR reporter activity. miR-214-positive A2780CP (left) and miR-214-negative HIOSE-80 cells (right) were transiently transfected with indicated plasmids. Following 36 h incubation, cells were subjected to luciferase assay. The data are the means of three independent experiments, and error bars indicate standard deviations. (F) Representative tumor and normal tissue lysates were analyzed by Western blot with indicated antibodies (panels 1 and 2). Expression of miR-214 was analyzed by qRT-PCR. (panel 3). U6 was used as a control (bottom panel).

FIG. 3A-FIG. 3D Ectopic expression of miR-214 induces ovarian cancer cells resistant to cisplatin induced apoptosis. (A) RNase protection analysis of miR-214 expression in ovarian cancer cell lines and immortalized human ovarian surface epithelial cells (top). 5S was used as control (bottom). (B) Ectopic expression of miR-214. A2780S and OV119 cells, which express low levels of endogenous miR-214, were transfected with pcDNA3.1N5-His-Topo-miR-214 or vector alone. Following 0418 selection, cells were subjected to qRT-PCR analysis for expression of miR-214 (top) and U6 (bottom). (C and D) Expression of miR-214 renders A2780S and OV119 cells resistant to cisplatin. The vector (Topo)- and miR-214-transfected cells were treated with cisplatin or DMSO for different time points. Cell viability was detected by MTT assay (C). After 48 h of the treatment, cells were labeled with Annexin V and analyzed by flow cytometry. (D).

DETAILED DESCRIPTION

Figures 1A, 1B:
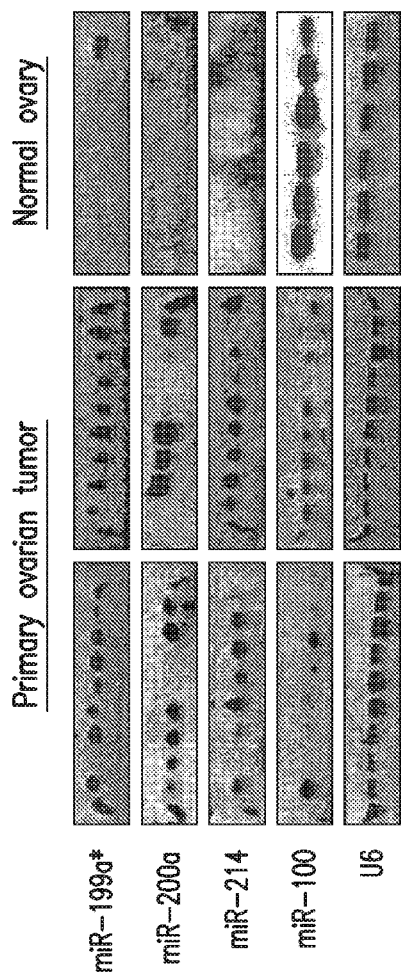
FIG. 1A-FIG. 1B miRNA expression profile and frequent deregulation of miR-199*, -200a, -214 and -100 in human primary ovarian cancer. (A) Northern blot analysis. Twenty IIg of total RNA from human primary ovarian tumors and normal ovary tissue were separated on a denaturing 15% polyacrilamide gel and transferred to a GeneScreen Plus membrane. The blot was hybridized with indicated probes. (B) List of deregulated miRNAs at more than I-fold in human ovarian cancer vs., normal ovary.

The inventors have determined, contrary to the prior art and experience, how to successfully use triciribine to treat ovarian cancer by one or a combination of (i) administering triciribine only to patients which according to a diagnostic test described below, exhibit enhanced sensitivity to the drug; (ii) using a described dosage level that minimizes the toxicity of the drug but yet still exhibits efficacy; or (iii) using a described dosage regimen that minimizes the toxicity of the drug.

Esophageal adenocarcinoma has demonstrated a rapid increase in incidence over the last 10 years. This increase mirrors a dramatic rise in that of Barrett esophagus, which is associated with esophageal adenocarcinoma in at least 95% of cases. In an attempt to understand the pathogenesis of esophageal adenocarcinoma, attention has turned to the antiapoptotic and oncogenic pathways. Here it is demonstrated that Akt was frequently activated in Barrett esophagus-related adenocarcinoma. Surprisingly, the levels of Akt activation were associated with tumor progression. After institutional review board ethics approval, 60 archival tissue specimens of esophageal adenocarcinoma arising on a background of Barrett esophagus were selected for immunohistochemical staining with phosphorylated Akt (p-Aid) antibody. The slides were scored by 2 independent observers. Approximately 80% of high-grade dysplasia and esophageal adenocarcinoma cases demonstrated strong to moderate Akt activity. Sixty-two percent of Barrett mucosa revealed low Akt activity, the remaining cases being p-Akt negative. None of the low-grade dysplasia cases exhibited strong p-Akt staining, whereas only weak p-Akt activity is seen in a portion of metaplastic Barrett mucosa, Akt is highly activated in high-grade dysplasia and esophageal adenocarcinoma arising from Barrett esophagus. These findings suggest a role of p-Akt in the progression of Barrett esophagus to esophageal adenocarcinoma and provide the rationale for using p-Akt inhibitor API-2/triciribine, which is currently in clinical trial, in the treatment of esophageal adenocarcinoma.

Compounds

The present invention provides for the use of TCN, TCN-P and related compounds for use in particular therapeutic regimens for the treatment of ovarian cancer.

In one embodiment, the compounds provided herein have the following structures:

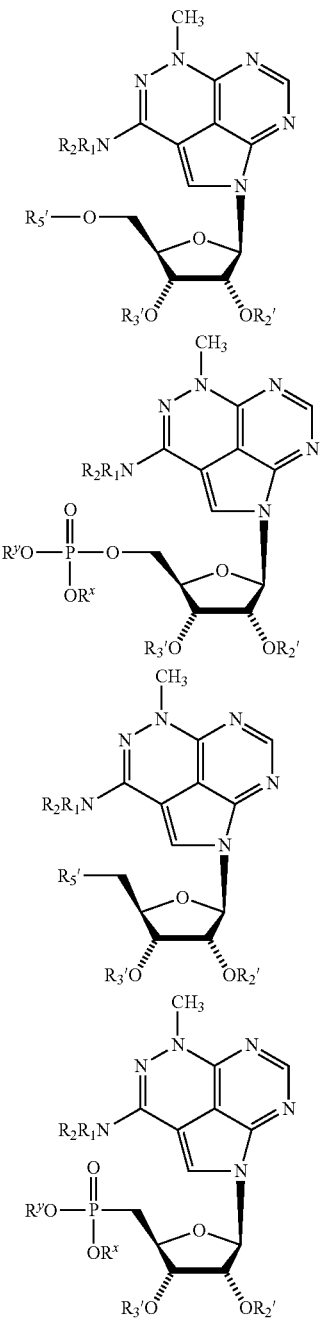

wherein each R2', R3' and R5' are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methanesulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate;

wherein $R^x$ and $R^y$ are independently hydrogen, optionally substituted phosphate; acyl (including lower acyl); amide, alkyl (including lower alkyl); aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

$R_1$ and $R_2$ each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl.

In one embodiment, R2' and R3' are hydrogen. In another embodiment, R2' and R5' are hydrogen. In yet another embodiment, R2', R3' and R5' are hydrogen. In yet another embodiment, R2', R3', R5', R1 and R2 are hydrogen.

In another embodiment, the compound has the following structure:

wherein $R_3$ is H, optionally substituted straight chained, branched or cyclic alkyl (including lower alkyl), alkenyl, or alkynyl, $NH_2$, $NHR^4$, $N(R^4)_2$, aryl, alkoxyalkyl, aryloxyalkyl, or substituted aryl; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl. In a subembodiment, $R_3$ is a straight chained C1-11 alkyl, iso-propyl, t-butyl, or phenyl.

In one embodiment, the compounds provided herein have the following structure:

-continued

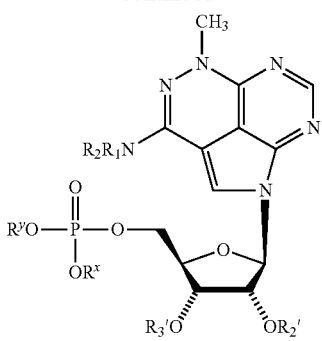

In another embodiment, the compounds provided herein have the following structure:

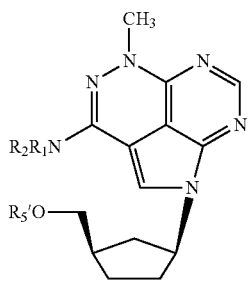

In another embodiment, the compounds provided herein have the following structure:

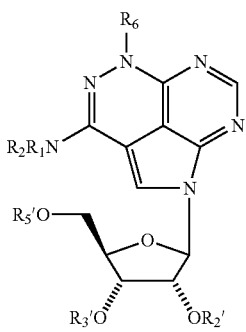

wherein $R_6$ is H, alkyl, (including lower alkyl) alkenyl, alkynyl, alkoxyalkyl, hydroxyalkyl, arylalkyl, cycloalkyl, $NH_2$, $NHR^4$, $NR^4R^4$, $CF_3$, $CH_2OH$, $CH_2F$, $CH_2Cl$, $CH_2CF_3$, $C(Y^3)_3$, $C(Y^3)_2C(Y^3)_3$, $C(=O)OH$, $C(=O)OR^4$, $C(=O)$-alkyl, $C(=O)$-aryl, $C(=O)$-alkoxyalkyl, $C(=O)NH_2$, $C(=O)NHR^4$, $C(=O)N(R^4)_2$, where each $Y^3$ is independently H or halo; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl.

In a subembodiment, $R_6$ is ethyl, $CH_2CH_2OH$, or $CH_2$-phenyl.

In another embodiment, the compounds provided herein have the following structure:

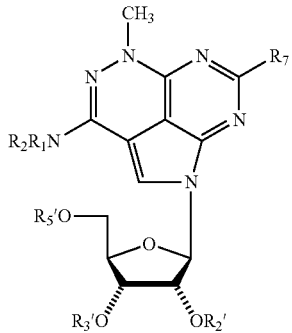

wherein $R_7$ is H, halo, alkyl (including lower alkyl), alkenyl, alkynyl, alkoxy, alkoxyalkyl, hydroxyalkyl, cycloalkyl, nitro, cyano, OH, $OR^4$, $NH_2$, $NHR^4$, $NR^4R^4$, SH, $SR^4$, $CF_3$, $CH_2OH$, $CH_2F$, $CH_2Cl$, $CH_2CF_3$, $C(Y^3)_3$, $C(Y^3)_2C(Y^3)_3$, $C(=O)OH$, $C(=O)OR^4$, $C(=O)$-alkyl, $C(=O)$-aryl, $C(=O)$-alkoxyalkyl, $C(=O)NH_2$, $C(=O)NHR^4$, $C(=O)N(R^4)_2$, or $N_3$, where each $Y^3$ is independently H or halo; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl.

In a subembodiment, $R_7$ is methyl, ethyl, phenyl, chloro or $NH_2$.

In another embodiment, the compounds provided herein have the following structure:

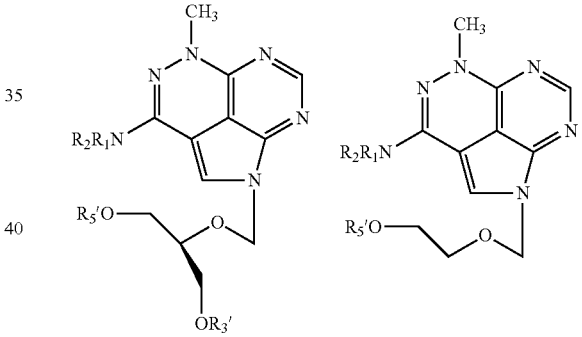

In another embodiment, the compounds provided herein have the following structure:

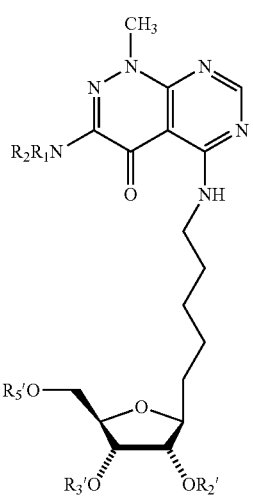

It is to be understood that the compounds disclosed herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the disclosure of a compound herein encompasses any racemic, optically active, polymorphic, or stereoisomeric form, or mixtures thereof, which preferably possesses the useful properties described herein, it being well known in the art how to prepare optically active forms and how to determine activity using the standard tests described herein, or using other similar tests which are will known in the art. Examples of methods that can be used to obtain optical isomers of the compounds include the following:

physical separation of crystals—a technique whereby macroscopic crystals of the individual enantiomers are manually separated. This technique can be used if crystals of the separate enantiomers exist, i.e., the material is a conglomerate, and the crystals are visually distinct;

simultaneous crystallization—a technique whereby the individual enantiomers are separately crystallized from a solution of the racemate, possible only if the latter is a conglomerate in the solid state;

enzymatic resolutions—a technique whereby partial or complete separation of a racemate by virtue of differing rates of reaction for the enantiomers with an enzyme enzymatic asymmetric synthesis—a synthetic technique whereby at least one step of the synthesis uses an enzymatic reaction to obtain an enantiomerically pure or enriched synthetic precursor of the desired enantiomer;

chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

enantiospecific synthesis from non-racemic precursors—a synthetic technique whereby the desired enantiomer is obtained from non-chiral starting materials and where the stereochemical integrity is not or is only minimally compromised over the course of the synthesis;

chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

chiral gas chromatography—a technique whereby the racemate is volatilized and enantiomers are separated by virtue of their differing interactions in the gaseous mobile phase with a column containing a fixed non-racemic chiral adsorbent phase;

extraction with chiral solvents—a technique whereby the enantiomers are separated by virtue of preferential dissolution of one enantiomer into a particular chiral solvent;

transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, triciribine, triciribine phosphate (TCN-P), triciribine 5'-phosphate (TCN-P), or the DMF adduct of triciribine (TCN-DMF) are provided. TCN can be synthesized by any technique known to one skilled in the art, for example, as described in Tetrahedron Letters, vol. 49, pp. 4757-4760 (1971). TCN-P can be prepared by any technique known to one skilled in the art, for example, as described in U.S. Pat. No. 4,123,524. The synthesis of TCN-DMF is described, for example, in INSERM, vol. 81, pp. 37-82 (1978). Other compounds related to TCN as described herein can be synthesized, for example, according to the methods disclosed in Gudmundsson, K. S., et al., "Synthesis of carbocyclic analogs of 2',3'-dideoxysangivamycin, 2',3'-dideoxytoyocamycin, and 2',3'-dideoxytriciribine," *Nucleosides Nucleotides Nucleic Acids*, 20(10-11):1823-1830 (October-November 2001); Porcari, A. R., et al., "6-N-Acyltriciribine analogues: structure-activity relationship between acyl carbon chain length and activity against HIV-1," *J. Med. Chem.*, 43(12):2457-2463 (Jun. 15, 2000); Porcari, A. R., et al., "Acyclic sugar analogs of triciribine: lack of antiviral and antiproliferative activity correlate with low intracellular phosphorylation," *Nucleosides Nucleotides*, 18(11-12):2475-2497 (November-December 1999), Porcari, A. R., et al., "Deoxy sugar analogues of triciribine: correlation of antiviral and antiproliferative activity with intracellular phosphorylation," *J. Med. Chem.*, 43(12):2438-2448 (Jun. 15, 2000), Porcari, A. R., et al., "Synthesis and antiviral activity of 2-substituted analogs of triciribine," *Nucleosides Nucleotides Nucleic Acids*, 22(12):2171-2193 (December 2003), Porcari, A. R., et al., "An improved total synthesis of triciribine: a tricyclic nucleoside with antineoplastic and antiviral properties," *Nucleosides Nucleotides Nucleic Acids*, 23(1-2):31-39 (2004), Schweinsberg, P. D., et al. "Identification of the metabolites of an antitumor tricyclic nucleoside (NSC-154020)," *Biochem. Pharmacol.*, 30(18):2521-2526 (Sep. 15, 1981)., Smith, K. L., et al., "Synthesis of new 2'-beta-C-methyl related triciribine analogues as anti-HCV agents," *Bioorg. Med. Chem. Lett.*, 14(13):3517-3520 (Jul. 5, 2004), Townsend, L. B., et al., "The synthesis and biological activity of certain pentaazaacenaphthylenes, hexaazaacenaphthylenes and their corresponding nucleosides," *Nucleic Acids Symp. Ser.*, 1986(17):41-44 (1986), and/or Wotring, L. L., et al., "Mechanism of activation of triciribine phosphate (TCN-P) as a prodrug form of TCN," *Cancer Treat Rep.*, 70(4):491-7 (April 1986).

Pharmaceutically Acceptable Salts and Prodrugs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleotides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

In one embodiment, the triciribine or a related compound is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin, et al.); U.S. Pat. No. 5,194,654 (Mar. 16, 1993, Hostetler, et al.); U.S. Pat. No. 5,223,263 (Jun. 29, 1993, Hostetler, et al.); U.S. Pat. No. 5,256,641 (Oct. 26, 1993, Yatvin, et al.); U.S. Pat. No. 5,411,947 (May 2, 1995, Hostetler, et al.); U.S. Pat. No. 5,463,092 (Oct. 31, 1995, Hostetler, et al.); U.S. Pat. No. 5,543,389 (Aug. 6, 1996, Yatvin, et al.); U.S. Pat. No. 5,543,390 (Aug. 6, 1996, Yatvin, et al.); U.S. Pat. No. 5,543,391 (Aug. 6, 1996, Yatvin, et al.); and U.S. Pat. No. 5,554,728 (Sep. 10, 1996, Basava, et al.), all of which are incorporated herein by reference.

Foreign patent applications that disclose lipophilic substituents that can be attached to the triciribine or a related compound s of the present invention, or lipophilic preparations, include WO 89/02733, WO 90/00555, WO 91/16920, WO 91/18914, WO 93/00910, WO 94/26273, WO/15132, EP 0 350 287, EP 93917054.4, and WO 91/19721.

Additional nonlimiting examples of derivatives of triciribine or a related compound s are those that contain substituents as described in the following publications. These derivatized triciribine or a related compound s can be used for the indications described in the text or otherwise as antiviral agents, including as anti-HIV or anti-HBV agents.

Ho, D. H. W. (1973) Distribution of Kinase and deaminase of 1β-D-arabinofuranosylcytosine in tissues of man and mouse. *Cancer Res.* 33, 2816-2820; Holy, A. (1993) Isopolar phosphorous-modified nucleotide analogues. In: De Clercq (ed.), Advances in Antiviral Drug Design, Vol. I, JAI Press, pp. 179-231; Hong, C. I., Nechaev, A., and West, C. R. (1979a) Synthesis and antitumor activity of 1β-3-arabinofuranosylcytosine conjugates of cortisol and cortisone. *Biochem. Biophys. Rs. Commun.* 88, 1223-1229; Hong, C. I., Nechaev, A., Kirisits, A. J. Buchheit, D. J. and West, C. R. (1980) Nucleoside conjugates as potential antitumor agents. 3. Synthesis and antitumor activity of 1-(β-D-arabinofuranosyl)cytosine conjugates of corticosteriods and selected lipophilic alcohols. *J. Med. Chem.* 28, 171-177; Hostetler, K. Y., Stuhmiller, L. M., Lenting, H. B. M. van den Bosch, H. and Richman, D. D. (1990) Synthesis and antiretroviral activity of phospholipid analogs of azidothymidine and other antiviral nucleosides. *J. Biol. Chem.* 266, 11714-11717; Hostetler, K. Y., Korba, B. Sridhar, C., Gardener, M. (1994a) Antiviral activity of phosphatidyl-dideoxycytidine in hepatitis B-infected cells and enhanced hepatic uptake in mice. *Antiviral Res.* 24, 59-67; Hostetler, K. Y., Richman, D. D., Sridhar, C. N. Felgner, P. L., Felgner, J., Ricci, J., Gerdener, M. F. Selleseth, D. W. and Ellis, M. N. (1994b) Phosphatidylazidothymidine and phosphatidyl-ddC: Assessment of uptake in mouse lymphoid tissues and antiviral activities in human immunodeficiency virus-infected cells and in rauscher leukemia virus-infected mice. *Antimicrobial Agents Chemother* 38, 2792-2797; Hunston, R. N., Jones, A. A. McGuigan, C., Walker, R. T., Balzarini, J., and De Clercq, E. (1984) Synthesis and biological properties of some cyclic phosphotriesters derived from 2'-deoxy-5-fluorouridine. *J. Med. Chem.* 27, 440-444; Ji, Y. H., Moog, C., Schmitt, G, Bischoff, P. and Luu, B. (1990); Monophosphoric acid diesters of 7β-hydroxycholesterol and of pyrimidine nucleosides as potential antitumor agents; synthesis and preliminary evaluation of antitumor activity. *J. Med. Chem.* 33, 2264-2270; Jones, A. S., McGuigan, C., Walter, R. T., Balzarini, J. and DeClercq, E. (1984) Synthesis, properties, and biological activity of some nucleoside cyclic phosphoramidates. *J. Chem. Soc.* Perkin Trans. I, 1471-1474; Juodka, B. A. and Smart, J. (1974) Synthesis of ditribonucleoside a (P N) amino acid derivatives. Coll. Czech. Chem. Comm. 39, 363-968; Kataoka, S., Imai, J., Yamaji, N., Kato, M., Saito, M., Kawada, T. and Imai, S. (1989) Alkylacted cAMP derivatives; selective synthesis and biological activities. *Nucleic Acids Res. Sym. Ser.*, 21, 1-2; Kataoka, S., Uchida, R. and Yamaji, N. (1991) A convenient synthesis of adenosine 3',5' cyclic phosphate (cAMP) benzyl and methyl triesters. *Heterocycles* 32, 1351-1356; Kinchington, D., Harvey, J. J., O'Connor, T. J., Jones, B. C. N. M., Devine, K. G, Taylor-Robinson, D., Jeffries, D. J. and McGuigan, C. (1992) Comparison of antiviral effects of zidovudine phosphoramidate and phosphorodiamidate derivatives against HIV and ULV in vitro. Antiviral Chem. Chemother. 3, 107-112; Kodama, K., Morozumi, M., Saitoh, K. I., Kuninaka, H., Yoshino, H. and Saneyoshi, M. (1989) Antitumor activity and pharmacology of 1-β-D-arabinofuranosylcytosine-5'-stearylphosphate; an orally active derivative of 1-β-D-arabinofuranosylcytosine. Jpn. J. *Cancer Res.* 80, 679-685; Korty, M. and Engels, J. (1979) The effects of adenosine- and guanosine 3',5'-phosphoric and acid benzyl esters on guinea-pig ventricular myocardium. Naunyn-Schmiedeberg's Arch. Pharmacol. 310, 103-111; Kumar, A., Goe, P. L., Jones, A. S. Walker, R. T. Balzarini, J. and De Clercq, E. (1990) Synthesis and biological evaluation of some cyclic phosphoramidate nucleoside derivatives. *J.*

Med. Chem. 33, 2368-2375; LeBec, C., and Huynh-dinh, T. (1991) Synthesis of lipophilic phosphate triester derivatives of 5-fluorouridine and arabinocytidine as anticancer prodrugs. *Tetrahedron Lett.* 32, 6553-6556; Lichtenstein, J., Barner, H. D. and Cohen S. S. (1960) The metabolism of exogenously supplied nucleotides by *Escherichia coli., J. Biol. Chem.* 235, 457-465; Lucthy, J., Von Daeniken, A., Friederich, J. Manthey, B., Zweifel, J., Schlatter, C. and Benn, M. H. (1981) Synthesis and toxicological properties of three naturally occurring cyanoepithioalkanes. Mitt. Geg. Lebensmittelunters. *Hyg.* 72, 131-133 (*Chem. Abstr.* 95, 127093); McGuigan, C. Tollerfield, S. M. and Riley, P. A. (1989) Synthesis and biological evaluation of some phosphate triester derivatives of the anti-viral drug Ara. *Nucleic Acids Res.* 17, 6065-6075; McGuigan, C., Devine, K. G., O'Connor, T. J., Galpin, S. A., Jeffries, D. J. and Kinchington, D. (1990a) Synthesis and evaluation of some novel phosphoramidate derivatives of 3'-azido-3'-deoxythymidine (AZT) as anti-HIV compounds. *Antiviral Chem. Chemother* 1, 107-113; McGuigan, C., O'Connor, T. J., Nicholls, S. R. Nickson, C. and Kinchington, D. (1990b) Synthesis and anti-HIV activity of some novel substituted dialkyl phosphate derivatives of AZT and ddCyd. *Antiviral Chem. Chemother* 1, 355-360; McGuigan, C., Nicholls, S. R., O'Connor, T. J., and Kinchington, D. (1990c) Synthesis of some novel dialkyl phosphate derivative of 3'-modified nucleosides as potential anti-AIDS drugs. Antiviral Chem. Chemother 1, 25-33; McGuigan, C., Devine, K. G, O'Connor, T. J., and Kinchington, D. (1991) Synthesis and anti-HIV activity of some haloalky phosphoramidate derivatives of 3'-azido-3'deoxythylmidine (AZT); potent activity of the trichloroethyl methoxyalaninyl compound. *Antiviral Res.* 15, 255-263; McGuigan, C., Pathirana, R. N., Mahmood, N., Devine, K. G. and Hay, A. J. (1992) Aryl phosphate derivatives of AZT retain activity against HIV1 in cell lines which are resistant to the action of AZT. *Antiviral Res.* 17, 311-321; McGuigan, C., Pathirana, R. N., Choi, S. M., Kinchington, D. and O'Connor, T. J. (1993a) Phosphoramidate derivatives of AZT as inhibitors of HIV; studies on the caroxyl terminus. *Antiviral Chem. Chemother* 4, 97-101; McGuigan, C., Pathirana, R. N., Balzarini, J. and De Clercq, E. (1993b) Intracellular delivery of bioactive AZT nucleotides by aryl phosphate derivatives of AZT. *J. Med. Chem.* 36, 1048-1052.

Alkyl hydrogen phosphonate derivatives of the anti-HIV agent AZT may be less toxic than the parent nucleoside analogue. *Antiviral Chem. Chemother.* 5, 271-277; Meyer, R. B., Jr., Shuman, D. A. and Robins, R. K. (1973) Synthesis of purine nucleoside 3',5'-cyclic phosphoramidates. *Tetrahedron Lett.* 269-272; Nagyvary, J. Gohil, R. N., Kirchner, C. R. and Stevens, J. D. (1973) Studies on neutral esters of cyclic AMP, *Biochem. Biophys. Res. Commun.* 55, 1072-1077; Namane, A. Goyette, C., Fillion, M. P., Fillion, G and Huynh-Dinh, T. (1992) Improved brain delivery of AZT using a glycosyl phosphotriester prodrug. *J. Med. Chem.* 35, 3939-3044; Nargeot, J. Nerbonne, J. M. Engels, J. and Leser, H. A. (1983) Natl. Acad. Sci. U.S.A. 80, 2395-2399; Nelson, K. A., Bentrude, W. G, Stser, W. N. and Hutchinson, J. P. (1987) The question of chair-twist equilibria for the phosphate rings of nucleoside cyclic 3',5'-monophosphates. $^1$HNMR and x-ray crystallographic study of the diasteromers of thymidine phenyl cyclic 3',5'-monophosphate. J. Am. Chem. Soc. 109, 4058-4064; Nerbonne, J. M., Richard, S., Nargeot, J. and Lester, H. A. (1984) New photoactivatable cyclic nucleotides produce intracellular jumps in cyclic AMP and cyclic GMP concentrations. Nature 301, 74-76; Neumann, J. M., Hervè, M., Debouzy, J. C., Guerra, F. I., Gouyette, C., Dupraz, B. and Huynh-Dinh, T. (1989) Synthesis and transmembrane transport studies by NMR of a glucosyl phospholipid of thymidine. J. Am. Chem. Soc. 111, 4270-4277; Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. (1991) Treatment of myelodyspastic syndromes with orally administered 1-β-D-rabinofuranosylcytosine-5'-stearylphosphate. Oncology 48, 451-455. Palomino, E., Kessle, D. and Horwitz, J. P. (1989) A dihydropyridine carrier system for sustained delivery of 2',3' dideoxynucleosides to the brain. J. Med. Chem. 32, 622-625; Perkins, R. M., Barney, S., Wittrock, R., Clark, P. H., Levin, R. Lambert, D. M., Petteway, S. R., Serafinowska, H. T., Bailey, S. M., Jackson, S., Harnden, M. R., Ashton, R., Sutton, D., Harvey, J. J. and Brown, A. G. (1993) Activity of BRL47923 and its oral prodrug, SB203657A against a rauscher murine leukemia virus infection in mice. Antiviral Res. 20 (Suppl. I). 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) Synthesis and evaluation of novel ether lipid nucleoside conjugates for anti-HIV-1 activity. J. Med. Chem. 34, 1408-1414; Pompon, A., Lefebvre, I., Imbach, J. L., Kahn, S. and Farquhar, D. (1994) Decomposition pathways of the mono- and bis(pivaloyloxymethyl) esters of azidothymidine-5'-monophosphate in cell extract and in tissue culture medium; an application of the on-line ISRP-cleaning' HPLC technique. Antiviral Chem. Chemother. 5, 91-98; Postemark, T. (1974) Cyclic AMP and cyclic GMP. Anu. Rev. Pharmacol. 14, 23-33; Prisbe, E. J., Martin, J. C. M., McGee, D. P. C., Barker, M. F., Smee, D. F. Duke, A. E., Matthews, T. R. and Verheyden, J. P. J. (1986) Synthesis and antiherpes virus activity of phosphate and phosphonate derivatives of 9-[(1,3-dihydroxy-2-propoxy)methyl]guanine. J. Med. Chem. 29, 671-675; Pucch, F., Gosselin, G, Lefebvre, I., Pompon, A., Aubertin, A. M. Dim, A. and Imbach, J. L. (1993) Intracellular delivery of nucleoside monophosphate through a reductase-mediated activation process. Antiviral Res. 22, 155-174; Pugaeva, V. P., Kochkeva, S. I., Mashbits, F. D. and Eizengart, R. S. (1969). Toxicological assessment and health standard ratings for ethylene sulfide in the industrial atmosphere. Gig. Trf. Prof Zabol. 13, 47-48 (Chem. Abstr. 72, 212); Robins, R. K. (1984) The potential of nucleotide analogs as inhibitors of retroviruses and tumors. Pharm. Res. 11-18; Rosowsky, A., Kim, S. H., Ross and J. Wick, M. M. (1982) Lipophilic 5'-(alkylphosphate) esters of 1-β-D-arabinofuranosylcyto-sine and its $N^4$-acyl and 2,2'-anhydro-3'0-acyl derivatives as potential prodrugs. J. Med. Chem. 25, 171-178; Ross, W. (1961) Increased sensitivity of the walker turnout towards aromatic nitrogen mustards carrying basic side chains following glucose pretreatment. Biochem. Pharm. 8, 235-240; Ryu, E. K., Ross, R. J., Matsushita, T., MacCoss, M., Hong, C. I. and West, C. R. (1982). Phospholipid-nucleoside conjugates 3. Synthesis and preliminary biological evaluation of 1-β-D-arabinofuranosylcytosine 5'diphosphate[−], 2-diacylglycerols. J. Med. Chem. 25, 1322-1329; Saffhill, R. and Hume, W. J. (1986) The degradation of 5-iododeoxyurindine and 5-bromoeoxyuridine by serum from different sources and its consequences for the use of these compounds for incorporation into DNA. Chem. Biol. Interact. 57, 347-355; Saneyoshi, M., Morozumi, M., Kodama, K., Machida, J., Kuninaka, A. and Yoshino, H. (1980) Synthetic nucleosides and nucleotides XVI. Synthesis and biological evaluations of a series of 1-β-D-arabinofuranosylcytosine 5'-alkyl or arylphosphates. Chem. Pharm. Bull. 28, 2915-2923; Sastry, J. K., Nehete, P. N., Khan, S., Nowak, B. J., Plunkett, W., Arlinghaus, R. B. and Farquhar, D. (1992) Membrane-permeable dideoxyuridine 5'-monophosphate analogue inhibits human immunodeficiency virus infection. Mol. Pharmacol. 41, 441-445; Shaw, J. P., Jones, R. J. Arimilli, M. N., Louie, M. S., Lee, W. A. and Cundy, K. C. (1994) Oral bioavailability of PMEA from PMEA prodrugs in male Sprague-Dawley rats. 9th Annual AAPS Meeting. San Diego, Calif. (Abstract). Shuto, S., Ueda, S., Imamura, S., Fukukuawa, K. Matsuda, A. and Ueda, T. (1987) A facile one-step synthesis of 5'-phosphatidylnucleosides by an enzymatic two-phase reaction. Tetrahedron Lett. 28, 199-202; Shuto, S., Itoh, H., Ueda, S., Imamura, S., Kukukawa, K., Tsujino, M. Matsuda, A. and Ueda, T. (1988) A facile enzymatic synthesis of 5'-(3-sn-phosphatidyl)nucleosides and their antileukemic activities. Chem. Pharm. Bull. 36, 209-217. One preferred phosphate prodrug group is the S-acyl-2-thioethyl group, also referred to as "SATE."

Additional examples of prodrugs that can be used are those described in the following patents and patent applications: U.S. Pat. Nos. 5,614,548, 5,512,671, 5,770,584, 5,962,437, 5,223,263, 5,817,638, 6,252,060, 6,448,392, 5,411,947, 5,744,592, 5,484,809, 5,827,831, 5,696,277, 6,022,029, 5,780,617, 5,194,654, 5,463,092, 5,744,461, 4,444,766, 4,562,179, 4,599,205, 4,493,832, 4,221,732, 5,116,992, 6,429,227, 5,149,794, 5,703,063, 5,888,990, 4,810,697, 5,512,671, 6,030,960, 2004/0259845, U.S. Pat. No. 6,670,341, 2004/0161398, 2002/082242, U.S. Pat. No. 5,512,671, 2002/0082242, and or PCT Publication Nos WO 90/11079, WO 96/39197, and/or WO 93/08807.

Definitions

As used herein, the terms "cancer" and "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

The term alkyl, as used herein, unless otherwise specified, includes a saturated straight, branched, or cyclic, primary, secondary, or tertiary hydrocarbon of for example $C_1$ to $C_{24}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl is optionally substituted, e.g., with one or more substituents such as halo (F, Cl, Br or I), (e.g. $CF_3$, 2-Br-ethyl, $CH_2F$, $CH_2Cl$, $CH_2CF_3$ or $CF_2CF_3$), hydroxyl (e.g. $CH_2OH$), amino (e.g. $CH_2NH_2$, $CH_2NHCH_3$ or $CH_2N(CH_3)_2$), alkylamino, arylamino, alkoxy, aryloxy, nitro, azido (e.g. $CH_2N_3$), cyano (e.g. $CH_2CN$), sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms.

The term alkylamino or arylamino includes an amino group that has one or two alkyl or aryl substituents, respectively.

The term amino acid includes naturally occurring and synthetic α, β, γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of a natural or synthetic amino acid including, but not limited to, α, β, γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "protected" as used herein and unless otherwise defined includes a group that is added to an oxygen, nitrogen, sulfur or phosphorus atom to prevent its further reaction or for other purposes. A wide variety of oxygen and nitrogen protecting groups are known to those skilled in the art of organic synthesis (see Greene and Wuts, *Protective Groups in Organic Synthesis*, $3^{rd}$ Ed., John Wiley & Sons, Inc., New York, N.Y., 1999).

The term aryl, as used herein, and unless otherwise specified, includes phenyl, biphenyl, or naphthyl, and preferably phenyl. The aryl group is optionally substituted with one or more moieties such as halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, 3$^{rd}$ Ed., 1999.

The term alkaryl or alkylaryl includes an alkyl group with an aryl substituent. The term aralkyl or arylalkyl includes an aryl group with an alkyl substituent.

The term halo, as used herein, includes chloro, bromo, iodo, and fluoro.

The term acyl includes a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

As used herein, the term "substantially free of" or "substantially in the absence of" with respect to enantiomeric purity, refers to a composition that includes at least 85% or 90% by weight, preferably 95% to 98% by weight, and even more preferably 99% to 100% by weight, of the designated enantiomer. In a preferred embodiment, in the methods and compounds of this invention, the compounds are substantially free of other enantiomers.

Similarly, the term "isolated" refers to a compound composition that includes at least 85% or 90% by weight, preferably 95% to 98% by weight, and even more preferably 99% to 100% by weight, of the compound, the remainder comprising other chemical species or enantiomers.

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term "pharmaceutically acceptable salt or prodrug" is used throughout the specification to describe any pharmaceutically acceptable form (such as an ester, phosphate ester, salt of an ester or a related group) of a compound, which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "pharmaceutically acceptable esters" as used herein, unless otherwise specified, includes those esters of one or more compounds, which are, within the scope of sound medical judgment, suitable for use in contact with the tissues of hosts without undue toxicity, irritation, allergic response and the like, are commensurate with a reasonable benefit/risk ratio, and are effective for their intended use.

The term "subject" as used herein refers to an animal, preferably a mammal, most preferably a human. Mammals can include non-human mammals, including, but not limited to, pigs, sheep, goats, cows (bovine), deer, mules, horses, monkeys and other non-human primates, dogs, cats, rats, mice, rabbits or any other known or disclosed herein.

II. In Vivo Efficacy/Dosing Regimens

In another aspect of the present invention, dosing regimens are provided that limit the toxic side effects of TCN and related compounds. In one embodiment, such dosing regimens minimize the following toxic side effects, including, but not limited to, hepatoxicity, thrombocytopenia, hyperglycemia, vomiting, hypocalcemia, anemia, hypoalbunemia, myelosuppression, hypertriglyceridemia, hyperamylasemia, diarrhea, stomachitis and/or fever.

In another embodiment, the administration of TCN, TCN-P or related compounds provides at least a partial or complete response in vivo in at least 15-20% of the subjects. In particular embodiments, a partial response can be at least 15, 20, 25, 30, 35, 40, 50, 55, 60, 65, 70, 75, 80 or 85% regression of the tumor. In other embodiments, this response can be evident in at least 15, 15, 20, 25, 30, 35, 40, 50, 55, 60, 65, 70, 75, 80, 85 or 90% of the subjects treated with the therapy. In further embodiments, such response rates can be obtained by any therapeutic regimen disclosed herein.

In other embodiments, methods are provided to treat a subject that has been diagnosed with ovarian cancer by administering to the subject an effective amount of TCN, TCN-P or a related compound according to a dosing schedule that includes administering the drug one time per week for three weeks followed by a one week period wherein the drug is not administered (i.e. via a 28 day cycle). In other embodiments, such 28 day cycles can be repeated at least 2, 3, 4, or 5 times or until regression of the tumor is evident.

In further embodiments, a 42 day cycle is provided in which the compounds disclosed herein can be administered once a week for four weeks followed by a two week period in which the drug is not administered. In other embodiments, such 42 day cycles can be repeated at least 2, 3, 4, or 5 times or until regression of the tumor is evident. In a particular embodiment, less than 12, less than 11 or less than 10 mg/m$^2$ of TCN, TCN-P or a related compound can be administered according to a 42 day cycle. In other particular embodiments, 2, 3, 4, 5, 6, 7, 8, 9, 10 or 11 mg/m$^2$ of TCN, TCN-P or a related compound can be administered according to a 42 day cycle.

In another embodiment, methods are provided to treat ovarian cancer in a subject by administering to the subject a dosing regimen of 10 mg/m$^2$ or less of TCN, TCN-P or a related compound one time per week. In particular embodiments, 0.5, 1, 1.5, 2, 2.5, 3, 3.5, 4, 4.5, 5, 5.5, 6, 6.5, 7, 7.5, 8, 8.5, 9, 9.5 or 10 mg/m$^2$ of TCN, TCN-P or a related compound as disclosed herein can be administered one time per week In embodiments of the present invention, the compound disclosed herein can be administered as a single bolus dose over a short period of time, for example, about 5, 10, 15, 20, 30 or 60 minutes. In further embodiments, dosing schedules are provided in which the compounds are administered via continuous infusion for at least 24, 48, 72, 96, or 120 hours. In certain embodiments, the administration of the drug via continuous or bolus infections can be repeated at a certain frequency at least: once a week, once every two weeks, once every three weeks, once a month, once every five weeks, once every six weeks, once every eight weeks, once every ten weeks and/or once every twelve weeks. The type and frequency of administrations can be combined ion any manner disclosed herein to create a dosing cycle. The drugs can be repeatedly administered via a certain dosing cycles, for example as a bolus injection once every two weeks for three months. The dosing cycles can be administered for at least: one, two three, four five, six, seven, eight, nine, ten, eleven, twelve, eighteen or twenty four months. Alternatively, at least 2, 3, 4, 5, 6, 7, 8, 9, 10, 11, 12, 15 or 20 dosing cycles can be administered to a patient. The drug can be administered according to any combination disclosed herein, for example, the drug can be administered once a week every three weeks for 3 cycles.

In further embodiments, the compounds can be administered at least once a day for at least 2, 3, 4, 5, 6, 7, 8, 9 or 10 days. Such administration can be followed by corresponding periods in which the drug is not administered.

The TCN, TCN-P and related compounds as disclosed herein can be administered to patients in an amount that is effective in causing tumor regression. The administration of TCN, TCN-P or related compounds can provide at least a partial, such as at least 15, 20 or 30%, or complete response in vivo in at least 15-20% of the subjects. In certain embodiments, at least 2, 5, 10, 15, 20, 30 or 50 mg/m$^2$ of a compound disclosed herein can be administered to a subject. In certain embodiments, at least about 0.5, 1, 1.5, 2, 2.5, 3, 3.5, 4, 4.5, 5, 5.5, 6, 6.5, 7, 7.5, 8, 8.5, 9, 9.5, 10, 12, 15, 17, 20, 25, 30, 35, 40, 45, 50, 55, 60, 65, 70, 75, 80, 85, 90, 95, 100, 150, 165, 175, 200, 250, 300, or 350 mg/m$^2$ of TCN, TCN-P or a related compound disclosed herein can be administered to a subject.

The administration of the compound can be conducted according to any of the therapeutic regimens disclosed herein. In particular embodiments, the dosing regimen includes administering less than 20 mg/m$^2$ of TCN and related compounds. In one embodiment, less than 20 mg/m$^2$ of TCN or related compounds can be administered once a week. In further embodiments, 2 mg/m$^2$, 5 mg/m$^2$, 10 mg/m$^2$, and/or 15 mg/m$^2$ of TCN or a related compound can be administered to a subject. In another embodiment, less than 10 mg/m$^2$ can be administered to a subject via continuous infusion for at least five days. The present invention provides for any combination of dosing type, frequency, number of cycles and dosage amount disclosed herein.

III. Screening of Patient Populations

In another aspect of the present invention, methods are provided to identify ovarian cancer susceptible to the toxic effects of triciribine (TCN) and related compounds. In one embodiment, methods are provided to ovarian cancer in a mammal by (i) obtaining a biological sample from the tumor; (ii) determining whether the cancer or tumor overexpresses Akt kinase or hyperactivated and phosphorylated Akt kinase, and (iii) treating the cancer or tumor with triciribine or a related compound as described herein. In one embodiment, the biological sample can be a biopsy. In other embodiments, the biological sample can be fluid, cells and/or aspirates obtained from the tumor or cancer.

The biological sample can be obtained according to any technique known to one skilled in the art. In one embodiment, a biopsy can be conducted to obtain the biological sample. A biopsy is a procedure performed to remove tissue or cells from the body for examination. Some biopsies can be performed in a physician's office, while others need to be done in a hospital setting. In addition, some biopsies require use of an anesthetic to numb the area, while others do not require any sedation. In certain embodiments, an endoscopic biopsy can be performed. This type of biopsy is performed through a fiberoptic endoscope (a long, thin tube that has a close-focusing telescope on the end for viewing) through a natural body orifice (i.e., mouth) or a small incision (i.e., arthroscopy). The endoscope is used to view the organ in question for abnormal or suspicious areas, in order to obtain a small amount of tissue for study. Endoscopic procedures are named for the organ or body area to be visualized and/or treated. The physician can insert the endoscope into the gastrointestinal tract (alimentary tract endoscopy), bladder (cystoscopy), abdominal cavity (laparoscopy), joint cavity (arthroscopy), mid-portion of the chest (mediastinoscopy), or trachea and bronchial system (laryngoscopy and bronchoscopy).

In another embodiment, a bone marrow biopsy can be performed. This type of biopsy can be performed either from the sternum (breastbone) or the iliac crest hipbone (the bone area on either side of the pelvis on the lower back area). The skin is cleansed and a local anesthetic is given to numb the area. A long, rigid needle is inserted into the marrow, and cells are aspirated for study; this step is occasionally uncomfortable. A core biopsy (removing a small bone 'chip' from the marrow) may follow the aspiration.

In a further embodiment, an excisional or incisional biopsy can be performed on the mammal. This type of biopsy is often used when a wider or deeper portion of the skin is needed. Using a scalpel (surgical knife), a full thickness of skin is removed for further examination, and the wound is sutured (sewed shut with surgical thread). When the entire tumor is removed, it is referred to as an excisional biopsy technique. If only a portion of the tumor is removed, it is referred to as an incisional biopsy technique. Excisional biopsy is often the method usually preferred, for example, when melanoma (a type of skin cancer) is suspected.

In still further embodiments, a fine needle aspiration (FNA) biopsy can be used. This type of biopsy involves using a thin needle to remove very small pieces from a tumor. Local anesthetic is sometimes used to numb the area, but the test rarely causes much discomfort and leaves no scar. FNA is not, for example, used for diagnosis of a suspicious mole, but may be used, for example, to biopsy large lymph nodes near a melanoma to see if the melanoma has metastasized (spread). A computed tomography scan (CT or CAT scan) can be used to guide a needle into a tumor in an internal organ such as the lung or liver.

In other embodiments, punch shave and/or skin biopsies can be conducted. Punch biopsies involve taking a deeper sample of skin with a biopsy instrument that removes a short cylinder, or "apple core," of tissue. After a local anesthetic is administered, the instrument is rotated on the surface of the skin until it cuts through all the layers, including the dermis, epidermis, and the most superficial parts of the subcutis (fat). A shave biopsy involves removing the top layers of skin by shaving it off. Shave biopsies are also performed with a local anesthetic. Skin biopsies involve removing a sample of skin for examination under the microscope to determine if, for example, melanoma is present. The biopsy is performed under local anesthesia.

In particular embodiment, methods are provided to determine whether the tumor overexpresses an Akt kinase. Akt kinase overexpression can refer to the phosphorylation state of the kinase. Hyperphosphorylation of Akt can be detected according to the methods described herein. In one embodiment, a tumor biopsy can be compared to a control tissue. The control tissue can be a normal tissue from the mammal in which the biopsy was obtained or a normal tissue from a healthy mammal Akt kinase overexpression or hyperphosphorylation can be determined if the tumor biopsy contains greater amounts of Akt kinase and/or Akt kinase phosphorylation than the control tissue, such as, for example, at least approximately 1.5, 2, 2.25, 2.5, 2.75, 3, 3.25, 3.5, 3.75, 4, 4.25, 4.5, 4.75, 5, 5.5, 6, 7, 8, 9, or 10-fold greater amounts of Akt kinase than contained in the control tissue.

In one embodiment, the present invention provides a method to detect aberrant Akt kinase expression in a subject or in a biological sample from the subject by contacting cells, cell extracts, serum or other sample from the subjects or said biological sample with an immunointeractive molecule specific for an Akt kinase or antigenic portion thereof and screening for the level of immunointeractive molecule-Akt kinase complex formation, wherein an elevated presence of the complex relative to a normal cell is indicative of an aberrant cell that expresses or overexpresses Akt. In one example, cells or cell extracts can be screened immunologically for the presence of elevated levels of Akt kinase.

In an alternative embodiment, the aberrant expression of Akt in a cell is detected at the genetic level by screening for the level of expression of a gene encoding an Akt kinase wherein an elevated level of a transcriptional expression product (i.e. mRNA) compared to a normal cell is indicative of an aberrant cell. In certain embodiments, real-time PCR as well as other PCR procedures can be used to determine transcriptional activity. In one embodiment, mRNA can be obtained from cells of a subject or from a biological sample from a subject and cDNA optionally generated. The mRNA or cDNA can then be contacted with a genetic probe capable of hybridizing to and/or amplifying all or part of a nucleotide sequence encoding Akt kinase or its complementary nucleotide sequence and then the level of the mRNA or cDNA can be detected wherein the presence of elevated levels of the mRNA or cDNA compared to normal controls can be assessed.

Yet another embodiment of the present invention contemplates the use of an antibody, monoclonal or polyclonal, to Akt kinase in a quantitative or semi-quantitative diagnostic kit to determine relative levels of Akt kinase in suspected cancer cells from a patient, which can include all the reagents necessary to perform the assay. In one embodiment, a kit utilizing reagents and materials necessary to perform an ELISA assay is provided. Reagents can include, for example, washing buffer, antibody dilution buffer, blocking buffer, cell staining solution, developing solution, stop solution, anti-phospho-protein specific antibodies, anti-Pan protein specific antibodies, secondary antibodies, and distilled water. The kit can also include instructions for use and can optionally be automated or semi-automated or in a form which is compatible with automated machine or software. In one embodiment, a phosphor-ser-473 Akt antibody that detects the activated form of AKT (Akt phosphorylated at serine 474) can be utilized as the antibody in a diagnostic kit. See, for example, Yuan et al. (2000) "Frequent Activation of AKT2 and induction of apoptosis by inhibition of phosphinositide-3-OH kinase/Akt pathway in human ovarian cancer," Oncogene 19:2324-2330.

Akt Kinases

Akt, also named $PKB^3$, represents a subfamily of the serine/threonine kinase. Three members, AKT1, AKT2, and AKT3, have been identified in this subfamily. Akt is activated by extracellular stimuli in a PI3K-dependent manner (Datta, S. R., et al. Genes Dev. 13: 2905-2927, 1999). Full activation of Akt requires phosphorylation of $Thr^{308}$ in the activation loop and $Ser^{473}$ in the C-terminal activation domain. Akt is negatively regulated by PTEN tumor suppressor. Mutations in PTEN have been identified in various tumors, which lead to activation of Akt pathway (Datta, S. R., et al. Genes Dev. 13: 2905-2927, 1999). In addition, amplification, overexpression and/or activation of Akt have been detected in a number of human malignancies (Datta, S. R., et al. Genes Dev. 13: 2905-2927, 1999, Cheng, J. Q., and Nicosia, S. V. AKT signal transduction pathway in oncogenesis. In Schwab D, editor. Encyclopedic Reference of Cancer. Berlin Heidelberg and New York: Springer; 2001. pp 35-7). Ectopic expression of Akt, especially constitutively active Akt, induces cell survival and malignant transformation whereas inhibition of Akt activity stimulates apoptosis in a range of mammalian cells (Datta, S. R., et al. Genes Dev. 13: 2905-2927, 1999, Cheng, J. Q., and Nicosia, S. V. AKT signal transduction pathway in oncogenesis. In Schwab D, editor. Encyclopedic Reference of Cancer. Berlin Heidelberg and New York: Springer; 2001. pp 35-7, Sun, M., et al. Am. J. Path., 159: 431-437, 2001, Cheng, J. Q., et al. Oncogene, 14: 2793-2801, 1997). Further, activation of Akt has been shown to associate with tumor invasiveness and chemoresistance (West, K. A., et al. Drug Resist. Updat., 5: 234-248, 2002).

Activation of the Akt pathway plays a pivotal role in malignant transformation and chemoresistance by inducing cell survival, growth, migration, and angiogenesis. The present invention provides methods to determine levels of Akt kinase overexpression and/or hyperactivated and phosphorylated Akt kinase.

The Akt kinase can be any known Akt family kinase, or kinase related thereto, including, but not limited to Akt 1, Akt 2, Akt 3. The mRNA and amino acid sequences of human Akt1, Akt2, and Akt 3 are illustrated in FIGS. 6a-c, 7a-d, and 8a-c, respectively.

Diagnostic Assays

Immunological Assays

In one embodiment, a method is provided for detecting the aberrant expression of an Akt kinase in a cell in a mammal or in a biological sample from the mammal, by contacting cells, cell extracts or serum or other sample from the mammal or biological sample with an immunointeractive molecule specific for an Akt kinase or antigenic portion thereof and screening for the level of immunointeractive molecule-Akt kinase complex formations and determining whether an elevated presence of the complex relative to a normal cell is present.

The immunointeractive molecule can be a molecule having specificity and binding affinity for an Akt kinase or its antigenic parts or its homologs or derivatives thereof. In one embodiment, the immunointeractive molecule can be an immunoglobulin molecule. In other embodiments, the immunointeractive molecules can be an antibody fragments, single chain antibodies, and/or deimmunized molecules including humanized antibodies and T-cell associated antigen-binding molecules (TABMs). In one particular embodiment, the antibody can be a monoclonal antibody. In another particular embodiment, the antibody can be a polyclonal antibody. The immunointeractive molecule can exhibit specificity for an Akt kinase or more particularly an antigenic determinant or epitope on an Akt kinase. An antigenic determinant or epitope on an Akt kinase includes that part of the molecule to which an immune response is directed. The antigenic determinant or epitope can be a B-cell epitope or where appropriate a T-cell epitope. In one embodiment, the antibody is a phosphor-ser 473 Akt antibody.

One embodiment of the present invention provides a method for diagnosing the presence of cancer or cancer-like growth in a mammal, in which aberrant Akt activity is present, by contacting cells or cell extracts from the mammal or a biological sample from the subject with an Akt kinase-binding effective amount of an antibody having specificity for the Akt kinase or an antigenic determinant or epitope thereon and then quantitatively or qualitatively determining the level of an Akt kinase-antibody complex wherein the presence of elevated levels of said complex compared to a normal cell is determined Antibodies can be prepared by any of a number of means known to one skilled in the art. For example, for the detection of human Akt kinase, antibodies can be generally but not necessarily derived from non-human animals such as primates, livestock animals (e.g. sheep, cows, pigs, goats, horses), laboratory test animals (e.g. mice, rats, guinea pigs, rabbits) and/or companion animals (e.g. dogs, cats). Antibodies may also be recombinantly produced in prokaryotic or eukaryotic host cells. Generally, antibody based assays can be conducted in vitro on cell or tissue biopsies. However, if an antibody is suitably deimmunized or, in the case of human use, humanized, then the antibody can be labeled with, for example, a nuclear tag, administered to a patient and the site of nuclear label accumulation determined by radiological techniques. The Akt kinase antibody can be a cancer targeting agent. Accordingly, another embodiment of the present invention provides deimmunized forms of the antibodies for use in cancer imaging in human and non-human patients.

In general, for the generation of antibodies to an Akt kinase, the enzyme is required to be extracted from a biological sample whether this be from animal including human tissue or from cell culture if produced by recombinant means. The Akt kinase can be separated from the biological sample by any suitable means. For example, the separation may take advantage of any one or more of the Akt kinase's surface charge properties, size, density, biological activity and its affinity for another entity (e.g. another protein or chemical compound to which it binds or otherwise associates). Thus, for example, separation of the Akt kinase from the biological fluid can be achieved by any one or more of ultra-centrifugation, ion-exchange chromatography (e.g. anion exchange chromatography, cation exchange chromatography), electrophoresis (e.g. polyacrylamide gel electrophoresis, isoelectric focussing), size separation (e.g., gel filtration, ultra-filtration) and affinity-mediated separation (e.g. immunoaffinity separation including, but not limited to, magnetic bead separation such as Dynabead (trademark) separation, immunochromatography, immuno-precipitation). The separation of Akt kinase from the biological fluid can preserve conformational epitopes present on the kinase and, thus, suitably avoids techniques that cause denaturation of the enzyme. In a further embodiment, the kinase can be separated from the biological fluid using any one or more of affinity separation, gel filtration and/or ultra-filtration.

Immunization and subsequent production of monoclonal antibodies can be carried out using standard protocols known in the art, such as, for example, described by Kohler and Milstein (Kohler and Milstein, Nature 256: 495-499, 1975; Kohler and Milstein, Eur. J. Immunol. 6(7): 511-519, 1976), Coligan et al. ("Current Protocols in Immunology, John Wiley & Sons, Inc., 1991-1997) or Toyama et al. (Monoclonal Antibody, Experiment Manual", published by Kodansha Scientific, 1987). Essentially, an animal is immunized with an Akt kinase-containing biological fluid or fraction thereof or a recombinant form of Akt kinase by standard methods to produce antibody-producing cells, particularly antibody-producing somatic cells (e.g. B lymphocytes). These cells can then be removed from the immunized animal for immortalization. In certain embodiment, a fragment of an Akt kinase can be used to the generate antibodies. The fragment can be associated with a carrier. The carrier can be any substance of typically high molecular weight to which a non- or poorly immunogenic substance (e.g. a hapten) is naturally or artificially linked to enhance its immunogenicity.

Immortalization of antibody-producing cells can be carried out using methods which are well-known in the art. For example, the immortalization may be achieved by the transformation method using Epstein-Barr virus (EBV) (Kozbor et al., Methods in Enzymology 121: 140, 1986). In another embodiment, antibody-producing cells are immortalized using the cell fusion method (described in Coligan et al., 1991-1997, supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In a particular embodiment, mice spleen cells can be used. In other embodiments, rat, rabbit, sheep or goat cells can also be used. Specialized myeloma cell lines have been developed from lymphocytic tumours for use in hybridoma-producing fusion procedures (Kohler and Milstein, 1976, supra; Shulman et al., Nature 276: 269-270, 1978; Volk et al., J. Virol. 42(1): 220-227, 1982). Many myeloma cell lines can also be used for the production of fused cell hybrids, including, e.g. P3.times.63-Ag8, P3.times.63-AG8.653, P3/NS1-Ag4-1 (NS-1), Sp2/0-Ag14 and S194/5.XXO.Bu.1. The P3.times.63-Ag8 and NS-1 cell lines have been described by Kohler and Milstein (1976, supra). Shulman et al. (1978, supra) developed the Sp2/0-Ag14 myeloma line. The S194/5.XXO.Bu.1 line was reported by Trowbridge (J. Exp. Med. 148(1): 313-323, 1978). Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler and Milstein, 1975, supra; Kohler and Milstein, 1976, supra; Gefter et al., Somatic Cell Genet. 3: 231-236, 1977; Volk et al., 1982, supra). The fusion-promoting agents used by those investigators were Sendai virus and polyethylene glycol (PEG). In certain embodiments, means to select the fused cell hybrids from the remaining unfused cells, particularly the unfused myeloma cells, are provided. Generally, the selection of fused cell hybrids can be accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. (Monoclonal Antibodies and Hybridomas: A New Dimension in Biological Analyses, pp 376-384, Plenum Press, New York, 1980) and by FACS analysis (O'Reilly et al., Biotechniques 25: 824-830, 1998).

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumours that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines can then be tested for their specificity to detect the Akt kinase of interest by any suitable immuno-detection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target LIM kinase but which does not recognize non-target epitopes are identified and then directly cultured in vitro or injected into a histocompatible animal to form tumours and to produce, collect and purify the required antibodies.

The present invention provides, therefore, a method of detecting in a sample an Akt kinase or fragment, variant or derivative thereof comprising contacting the sample with an antibody or fragment or derivative thereof and detecting the level of a complex containing the antibody and Akt kinase or fragment, variant or derivative thereof compared to normal controls wherein elevated levels of Akt kinase is determined Any suitable technique for determining formation of the complex may be used. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) immunochromatographic techniques (ICTs), and Western blotting which are well known to those of skill in the art Immunoassays can also include competitive assays. The present invention encompasses qualitative and quantitative immunoassays.

Suitable immunoassay techniques are described, for example, in U.S. Pat. Nos. 4,016,043, 4,424,279 and 4,018,653. These include both single-site and two-site assays of the non-competitive types, as well as the traditional competitive binding assays. These assays also include direct binding of a labeled antigen-binding molecule to a target antigen.

The invention further provides methods for quantifying Akt protein expression and activation levels in cells or tissue samples obtained from an animal, such as a human cancer patient or an individual suspected of having cancer. In one embodiment, the invention provides methods for quantifying Akt protein expression or activation levels using an imaging system quantitatively. The imaging system can be used to receive, enhance, and process images of cells or tissue samples, that have been stained with AKT protein-specific stains, in order to determine the amount or activation level of AKT protein expressed in the cells or tissue samples from such an animal. In embodiments of the methods of the invention, a calibration curve of AKT1 and AKT2 protein expression can be generated for at least two cell lines expressing differing amounts of AKT protein. The calibration curve can then used to quantitatively determine the amount of AKT protein that is expressed in a cell or tissue sample. Analogous calibration curves can be made for activated AKT proteins using reagents specific for the activation features. It can also be used to determine changes in amounts and activation state of AKT before and after clinical cancer treatment.

In one particular embodiment of the methods of the invention, AKT protein expression in a cell or tissue sample can be quantified using an enzyme-linked immunoabsorbent assay (ELISA) to determine the amount of AKT protein in a sample. Such methods are described, for example, in U.S. Patent Publication No. 2002/0015974.

In other embodiments enzyme immunoassays can be used to detect the Akt kinase. In such assays, an enzyme is conjugated to the second antibody, generally by means of glutaraldehyde or periodate. The substrates to be used with the specific enzymes are generally chosen for the production of, upon hydrolysis by the corresponding enzyme, a detectable colour change. It is also possible to employ fluorogenic substrates, which yield a fluorescent product rather than the chromogenic substrates. The enzyme-labeled antibody can be added to the first antibody-antigen complex, allowed to bind, and then the excess reagent washed away. A solution containing the appropriate substrate can then be added to the complex of antibody-antigen-antibody. The substrate can react with the enzyme linked to the second antibody, giving a qualitative visual signal, which may be further quantitated, usually spectrophotometrically, to give an indication of the amount of antigen which was present in the sample. Alternately, fluorescent compounds, such as fluorescein, rhodamine and the lanthanide, europium (EU), can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent-labeled antibody is allowed to bind to the first antibody-antigen complex. After washing off the unbound reagent, the remaining tertiary complex is then exposed to light of an appropriate wavelength. The fluorescence observed indicates the presence of the antigen of interest Immunofluorometric assays (IFMA) are well established in the art and are particularly useful for the present method. However, other reporter molecules, such as radioisotope, chemiluminescent or bioluminescent molecules can also be employed.

In a particular embodiment, antibodies to Akt kinase can also be used in ELISA-mediated detection of Akt kinase especially in serum or other circulatory fluid. This can be accomplished by immobilizing anti-Akt kinase antibodies to a solid support and contacting these with a biological extract such as serum, blood, lymph or other bodily fluid, cell extract or cell biopsy. Labeled anti-Akt kinase antibodies can then be used to detect immobilized Akt kinase. This assay can be varied in any number of ways and all variations are encompassed by the present invention and known to one skilled in the art. This approach can enable rapid detection and quantitation of Akt kinase levels using, for example, a serum-based assay.

In one embodiment, an Akt Elisa assay kit may be used in the present invention. For example, a Cellular Activation of Signaling ELISA kit for Akt S473 from SuperArray Bioscience can be utilized in the present invention. In one embodiment, the antibody can be an anti-pan antibody that recognizes Akt S473. Elisa assay kit containing an anti-Akt antibody and additional reagents, including, but not limited to, washing buffer, antibody dilution buffer, blocking buffer, cell staining solution, developing solution, stop solution, secondary antibodies, and distilled water.

Nucleotide Detection

In another embodiment, a method to detect Akt kinases is provided by detecting the level of expression in a cell of a polynucleotide encoding an Akt kinase. Expression of the polynucleotide can be determined using any suitable technique known to one skilled in the art. In one embodiment, a labeled polynucleotide encoding an Akt kinase can be utilized as a probe in a Northern blot of an RNA extract obtained from the cell. In other embodiments, a nucleic acid extract from an animal can be utilized in concert with oligonucleotide primers corresponding to sense and anti-sense sequences of a polynucleotide encoding the kinase, or flanking sequences thereof, in a nucleic acid amplification reaction such as RT PCR. A variety of automated solid-phase detection techniques are also available to one skilled in the art, for example, as described by Fodor et al. (Science 251: 767-777, 1991) and Kazal et al. (Nature Medicine 2: 753-759, 1996).

In other embodiments, methods are provided to detect akt kinase encoding RNA transcripts. The RNA can be isolated from a cellular sample suspected of containing Akt kinase RNA, e.g. total RNA isolated from human cancer tissue. RNA can be isolated by methods known in the art, e.g. using TRIZOL reagent (GIBCO-BRL/Life Technologies, Gaithersburg, Md.). Oligo-dT, or random-sequence oligonucleotides, as well as sequence-specific oligonucleotides can be employed as a primer in a reverse transcriptase reaction to prepare first-strand cDNAs from the isolated RNA. Resultant first-strand cDNAs can then amplified with sequence-specific oligonucleotides in PCR reactions to yield an amplified product.

Polymerase chain reaction or "PCR" refers to a procedure or technique in which amounts of a preselected fragment of nucleic acid, RNA and/or DNA, are amplified as described, for example, in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences and cDNA transcribed from total cellular RNA. See generally Mullis et al. (Quant. Biol. 51: 263, 1987; Erlich, eds., PCR Technology, Stockton Press, NY, 1989). Thus, amplification of specific nucleic acid sequences by PCR relies upon oligonucleotides or "primers" having conserved nucleotide sequences wherein the conserved sequences are deduced from alignments of related gene or protein sequences, e.g. a sequence comparison of mammalian Akt kinase genes. For example, one primer is prepared which is predicted to anneal to the antisense strand and another primer prepared which is predicted to anneal to the sense strand of a cDNA molecule which encodes a Akt kinase. To detect the amplified product, the reaction mixture is typically subjected to agarose gel electrophoresis or other convenient separation technique and the relative presence of the Akt kinase specific amplified DNA detected. For example, Akt kinase amplified DNA may be detected using Southern hybridization with a specific oligonucleotide probe or comparing its electrophoretic mobility with DNA standards of known molecular weight. Isolation, purification and characterization of the amplified Akt kinase DNA can be accomplished by excising or eluting the fragment from the gel (for example, see references Lawn et al., Nucleic Acids Res. 2: 6103, 1981; Goeddel et al., Nucleic cids Res. 8: 4057-1980), cloning the amplified product into a cloning site of a suitable vector, such as the pCRII vector (Invitrogen), sequencing the cloned insert and comparing the DNA sequence to the known sequence of LIM kinase. The relative amounts of LIM kinase mRNA and cDNA can then be determined In one embodiment, real-time PCR can be used to determine transcriptional levels of Akt nucleotides. Determination of transcriptional activity also includes a measure of potential translational activity based on available mRNA transcripts. Real-time PCR as well as other PCR procedures use a number of chemistries for detection of PCR product including the binding of DNA binding fluorophores, the 5' endonuclease, adjacent liner and hairpin oligoprobes and the self-fluorescing amplicons. These chemistries and real-time PCR in general are discussed, for example, in Mackay et al., Nucleic Acids Res 30(6): 1292-1305, 2002; Walker, J. Biochem. Mol. Toxicology 15(3): 121-127, 2001; Lewis et al., J. Pathol. 195: 66-71, 2001.

In an alternate embodiment, the aberrant expression of Akt can be identified by contacting a nucleotide sequences isolated from a biological sample with an oligonucleotide probe having a sequence complementary to an Akt sequences selected from the nucleotide sequences of FIG. 6a-c, 7a-d, or 8a-c, or fragment thereof, and then detecting the sequence by hybridizing the probe to the sequence, and comparing the results to a normal sample. The hybridization of the probe to the biological sample can be detected by labeling the probe using any detectable agent. The probe can be labeled for example, with a radioisotope, or with biotin, fluorescent dye, electron-dense reagent, enzyme, hapten or protein for which antibodies are available. The detectable label can be assayed by any desired means, including spectroscopic, photochemical, biochemical, immunochemical, radioisotopic, or chemical means. The probe can also be detected using techniques such as an oligomer restriction technique, a dot blot assay, a reverse dot blot assay, a line probe assay, and a 5' nuclease assay. Alternatively, the probe can be detected using any of the generally applicable DNA array technologies, including macroarray, microarray and DNA microchip technologies. The oligonucleotide probe typically includes approximately at least 14, 15, 16, 18, 20, 25 or 28 nucleotides that hybridize to the nucleotides selected from FIGS. 6a-c, 7a-d, and 8a-c, or a fragment thereof. It is generally not preferred to use a probe that is greater than approximately 25 or 28 nucleotides in length. The oligonucleotide probe is designed to identify an Akt nucleotide sequence.

Kinase Assays

The activity of the Akt kinases can be measured using any suitable kinase assay known in the art. For example, and not by way of limitation, the methods described in Hogg et al (Oncogene 1994 9:98-96), Mills et al (J. Biol. Chem. 1992 267:16000-006) and Tomizawa et al 2001 (FEBS Lett. 2001 492: 221-7), Schmandt et al, (J. Immunol. 1994, 152:96-105) can be used. Further serine, threonine and tyrosine kinase assays are described in Ausubel et al. (Short Protocols in Molecular Biology, 1999, unit 17.6).

Akt kinase assays can generally use an Akt polypeptide, a labeled donor substrate, and a receptor substrate that is either specific or non-specific for Akt. In such assays Akt transfers a labeled moiety from the donor substrate to the receptor substrate, and kinase activity is measured by the amount of labeled moiety transferred from the donor substrate to the receptor substrate. Akt polypeptide can be produced using various expression systems, can be purified from cells, can be in the form of a cleaved or uncleaved recombinant fusion protein and/or can have non-Akt polypeptide sequences, for example a His tag or .beta.-galactosidase at its N- or C-terminus Akt activity can be assayed in cancerous cells lines if the cancerous cell lines are used as a source of the Akt to be assayed. Suitable donor substrates for Akt assays include any molecule that is susceptible to dephosphorylation by Akt., such as, for example include .gamma.-labeled ATP and ATP analogs, wherein the label is $^{33}$P, $^{32}$P, $^{35}$S or any other radioactive isotope or a suitable fluorescent marker. Suitable recipient substrates for Akt assays include any polypeptide or other molecule that is susceptible to phosphorylation by Akt. Recipient substrates can be derived from fragments of in vivo targets of Akt. Recipient substrates fragments can be 8 to 50 amino acids in length, usually 10 to 30 amino acids and particularly of about 10, 12, 15, 18, 20 and 25 amino acids in length. Further recipient substrates can be determined empirically using a set of different polypeptides or other molecules. Targets of Recipient substrates for TTK can be capable of being purified from other components of the reaction once the reaction has been performed. This purification is usually done through a molecular interaction, where the recipient substrates is biotinylated and purified through its interaction with streptavidin, or a specific antibody is available that can specifically recognize the recipient substrates. The reaction can be performed in a variety of conditions, such as on a solid support, in a gel, in solution or in living cells. The choice of detection methods depends on type of label used for the donor molecule and may include, for example, measurement of incorporated radiation or fluorescence by autoradiography, scintillation, scanning or fluorography.

IV. Methods of Treatment

The compounds and pharmaceutical compositions provided herein can be used in the treatment of ovarian cancer and other disorders associated with abnormal cell proliferation. In one embodiment, the compounds of the present invention can be used to treat ovarian cancer.

Drug Resistant Tumors or Cancers

The invention provides compounds that can be used to treat drug resistant ovarian cancer. In one embodiment, the compound, such as TCN, TCN-P or a related compound as disclosed herein, can be co-administered with a second drug.

Multidrug resistance (MDR) occurs in human cancers and can be a significant obstacle to the success of chemotherapy. Multidrug resistance is a phenomenon whereby tumor cells in vitro that have been exposed to one cytotoxic agent develop cross-resistance to a range of structurally and functionally unrelated compounds. In addition, MDR can occur intrinsically in some cancers without previous exposure to chemotherapy agents. Thus, in one embodiment, the present invention provides methods for the treatment of a patient with a drug resistant cancer, for example, multidrug resistant cancer, by administration of TCN, TCN-P or a related compound as disclosed herein. In certain embodiments, TCN, TCN-P and related compounds can be used to treat cancers that are resistant to taxol, rapamycin, tamoxifen, cisplatin, and/or gefitinib (iressa).

In one embodiment, TCN, TCN-P or a related compound as disclosed herein can be used for the treatment of drug resistant cancers of the colon, bone, kidney, adrenal, pancreas, liver and/or any other cancer known in the art or described herein.

Combination Therapy

In one aspect of the present invention, the compounds and compositions disclosed herein can be combined with at least one additional chemotherapeutic agent. The additional agents can be administered in combination or alternation with the compounds disclosed herein. The drugs can form part of the same composition, or be provided as a separate composition for administration at the same time or a different time.

In one embodiment, compounds disclosed herein can be combined with antiangiogenic agents to enhance their effectiveness, or combined with other antiangiogenic agents and administered together with other cytotoxic agents. In another embodiment, the compounds and compositions, when used in the treatment of solid tumors, can be administered with the agents selected from, but not limited to IL-12, retinoids, interferons, angiostatin, endostatin, thalidomide, thrombospondin-1, thrombospondin-2, captopryl, anti-neoplastic agents such as alpha interferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and radiation. In further embodiments, the compounds and compositions disclosed herein can be administered in combination or alternation with, for example, drugs with antimitotic effects, such as those which target cytoskeletal elements, including microtubule modulators such as taxane drugs (such as taxol, paclitaxel, taxotere, docetaxel), podophylotoxins or vinca alkaloids (vincristine, vinblastine); antimetabolite drugs (such as 5-fluorouracil, cytarabine, gemcitabine, purine analogues such as pentostatin, methotrexate); alkylating agents or nitrogen mustards (such as nitrosoureas, cyclophosphamide or ifosphamide); drugs which target DNA such as the antracycline drugs adriamycin, doxorubicin, pharmorubicin or epirubicin; drugs which target topoisomerases such as etoposide; hormones and hormone agonists or antagonists such as estrogens, antiestrogens (tamoxifen and related compounds) and androgens, flutamide, leuprorelin, goserelin, cyprotrone or octreotide; drugs which target signal transduction in tumour cells including antibody derivatives such as herceptin; alkylating drugs such as platinum drugs (cis-platin, carbonplatin, oxaliplatin, paraplatin) or nitrosoureas; drugs potentially affecting metastasis of tumours such as matrix metalloproteinase inhibitors; gene therapy and antisense agents; antibody therapeutics; other bioactive compounds of marine origin, notably the didemnins such as aplidine; steroid analogues, in particular dexamethasone; anti-inflammatory drugs, including non-steroidal agents (such as acetaminophen or ibuprofen) or steroids and their derivatives in particular dexamethasone; anti-emetic drugs, including 5HT-3 inhibitors (such as gramisetron or ondasetron), and steroids and their derivatives in particular dexamethasone. In still further embodiments, the compounds and compositions can be used in combination or alternation with the chemotherapeutic agents disclosed below in Table 1.

TABLE 1

Chemotherapeutic Agents

| | |
|---|---|
| 13-cis-Retinoic Acid | Neosar |
| 2-Amino-6-Mercaptopurine | Neulasta |
| 2-CdA | Neumega |
| 2-Chlorodeoxyadenosine | Neupogen |
| 5-fluorouracil | Nilandron |
| 5-FU | Nilutamide |
| 6 - TG | Nitrogen Mustard |
| 6 - Thioguanine | Novaldex |
| 6-Mercaptopurine | Novantrone |
| 6-MP | Octreotide |
| Accutane | Octreotide acetate |
| Actinomycin-D | Oncospar |
| Adriamycin | Oncovin |
| Adrucil | Ontak |
| Agrylin | Onxal |
| Ala-Cort | Oprevelkin |
| Aldesleukin | Orapred |
| Alemtuzumab | Orasone |
| Alitretinoin | Oxaliplatin |
| Alkaban-AQ | Paclitaxel |
| Alkeran | Pamidronate |
| All-transretinoic acid | Panretin |
| Alpha interferon | Paraplatin |
| Altretamine | Pediapred |
| Amethopterin | PEG Interferon |
| Amifostine | Pegaspargase |
| Aminoglutethimide | Pegfilgrastim |
| Anagrelide | PEG-INTRON |
| Anandron | PEG-L-asparaginase |
| Anastrozole | Phenylalanine Mustard |
| Arabinosylcytosine | Platinol |
| Ara-C | Platinol-AQ |
| Aranesp | Prednisolone |
| Aredia | Prednisone |
| Arimidex | Prelone |
| Aromasin | Procarbazine |
| Arsenic trioxide | PROCRIT |
| Asparaginase | Proleukin |
| ATRA | Prolifeprospan 20 with Carmustine implant |
| Avastin | |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | |
| Bleomycin | Rubex |
| Bortezomib | Rubidomycin hydrochloride |
| Busulfan | Sandostatin |
| Busulfex | Sandostatin LAR |
| C225 | Sargramostim |
| Calcium Leucovorin | Solu-Cortef |
| Campath | Solu-Medrol |
| Camptosar | STI-571 |
| Camptothecin-11 | Streptozocin |
| Capecitabine | Tamoxifen |
| Carac | Targretin |
| Carboplatin | Taxol |
| Carmustine | Taxotere |
| Carmustine wafer | Temodar |
| Casodex | Temozolomide |
| CCNU | Teniposide |
| CDDP | TESPA |
| CeeNU | Thalidomide |
| Cerubidine | Thalomid |
| cetuximab | TheraCys |
| Chlorambucil | Thioguanine |
| Cisplatin | Thioguanine Tabloid |
| Citrovorum Factor | Thiophosphoamide |
| Cladribine | Thioplex |
| Cortisone | Thiotepa |
| Cosmegen | TICE |
| CPT-11 | Toposar |
| Cyclophosphamide | Topotecan |
| Cytadren | Toremifene |
| Cytarabine | Trastuzumab |
| Cytarabine liposomal | Tretinoin |
| | Trexall |

TABLE 1-continued

Chemotherapeutic Agents

| | |
|---|---|
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| Daunorubicin liposomal | Vinblastine |
| DaunoXome | Vinblastine Sulfate |
| Decadron | Vincasar Pfs |
| Delta-Cortef | Vincristine |
| Deltasone | Vinorelbine |
| Denileukin diftitox | Vinorelbine tartrate |
| DepoCyt | VLB |
| Dexamethasone | VP-16 |
| Dexamethasone acetate | Vumon |
| dexamethasone sodium phosphate | Xeloda |
| | Zanosar |
| Dexasone | Zevalin |
| Dexrazoxane | Zinecard |
| DHAD | Zoladex |
| DIC | Zoledronic acid |
| Diodex | Zometa |
| Docetaxel | Gliadel wafer |
| Doxil | Glivec |
| Doxorubicin | GM-CSF |
| Doxorubicin liposomal | Goserelin |
| Droxia | granulocyte - colony stimulating factor |
| DTIC | Granulocyte macrophage colony stimulating factor |
| DTIC-Dome | |
| Duralone | Halotestin |
| Efudex | Herceptin |
| Eligard | Hexadrol |
| Ellence | Hexalen |
| Eloxatin | Hexamethylmelamine |
| Elspar | HMM |
| Emcyt | Hycamtin |
| Epirubicin | Hydrea |
| Epoetin alfa | Hydrocort Acetate |
| Erbitux | Hydrocortisone |
| *Erwinia* L-asparaginase | Hydrocortisone sodium phosphate |
| Estramustine | Hydrocortisone sodium succinate |
| Ethyol | Hydrocortone phosphate |
| Etopophos | Hydroxyurea |
| Etoposide | Ibritumomab |
| Etoposide phosphate | Ibritumomab Tiuxetan |
| Eulexin | Idamycin |
| Evista | Idarubicin |
| Exemestane | Ifex |
| Fareston | IFN-alpha |
| Faslodex | Ifosfamide |
| Femara | IL - 2 |
| Filgrastim | IL-11 |
| Floxuridine | Imatinib mesylate |
| Fludara | Imidazole Carboxamide |
| Fludarabine | Interferon alfa |
| Fluoroplex | Interferon Alfa-2b (PEG conjugate) |
| Fluorouracil | Interleukin - 2 |
| Fluorouracil (cream) | Interleukin-11 |
| Fluoxymesterone | Intron A (interferon alfa-2b) |
| Flutamide | Leucovorin |
| Folinic Acid | Leukeran |
| FUDR | Leukine |
| Fulvestrant | Leuprolide |
| G-CSF | Leurocristine |
| Gefitinib | Leustatin |
| Gemcitabine | Liposomal Ara-C |
| Gemtuzumab ozogamicin | Liquid Pred |
| Gemzar | Lomustine |
| Gleevec | L-PAM |
| Lupron | L-Sarcolysin |
| Lupron Depot | Meticorten |
| Matulane | Mitomycin |
| Maxidex | Mitomycin-C |
| Mechlorethamine | Mitoxantrone |
| Mechlorethamine Hydrochlorine | M-Prednisol |
| | MTC |

TABLE 1-continued

Chemotherapeutic Agents

| | |
|---|---|
| Medralone | MTX |
| Medrol | Mustargen |
| Megace | Mustine |
| Megestrol | Mutamycin |
| Megestrol Acetate | Myleran |
| Melphalan | Iressa |
| Mercaptopurine | Irinotecan |
| Mesna | Isotretinoin |
| Mesnex | Kidrolase |
| Methotrexate | Lanacort |
| Methotrexate Sodium | L-asparaginase |
| Methylprednisolone | LCR |
| Mylocel | |
| Letrozole | |

In certain embodiments, interferons (IFNs) can be used in combinations with the compounds of the present invention. Suitable intereferons include: interferon alpha-2a, interferon alpha-2b, pegylated interferon alpha, including interferon alpha-2a and interferon alpha 2b, interferon beta, interferon gamma, interferon tau, interferon omega, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and/or interferon gamma-1b by InterMune.

In one embodiment TCN, TCN-P or a related compound as disclosed herein can be used in combination or alternation with additional chemotherapeutic agents, such as those described herein or in Table 3, for the treatment of drug resistant cancer, for example multiple drug resistant cancer. Drug resistant cancers can include cancers of the colon, bone, kidney, adrenal, pancreas, liver and/or any other cancer known in the art or described herein. In one embodiment, the additional chemotherapeutic agent can be a P-glycoprotein inhibitor. In certain non-limiting embodiments, the P-glycoprotein inhibitor can be selected from the following drugs: verapamil, cyclosporin (such as cyclosporin A), tamoxifen, calmodulin antagonists, dexverapamil, dexniguldipine, valspodar (PSC 833), biricodar (VX-710), tariquidar (XR9576), zosuquidar (LY335979), laniquidar (R101933), and/or ONT-093.

V. Pharmaceutical Compositions

Pharmaceutical carriers suitable for administration of the compounds provided herein include any such carriers known to those skilled in the art to be suitable for the particular mode of administration. The compounds may be formulated as the sole pharmaceutically active ingredient in the composition or may be combined with other active ingredients.

Compositions comprising the compounds disclosed herein may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

The compositions may conveniently be presented in unit dosage form and may be prepared by conventional pharmaceutical techniques. Such techniques include the step of bringing into association one or more compositions of the present invention and one or more pharmaceutical carriers or excipients.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof may be mixed with one or more suitable pharmaceutical carriers. The compounds may be derivatized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa., 15th Edition, 1975.

Compositions of the present invention suitable for topical administration in the mouth include for example, lozenges, having the ingredients in a flavored basis, usually sucrose and acacia or tragacanth; pastilles, having one or more of the compositions of the present invention in an inert basis such as gelatin and glycerin, or sucrose and acacia; and mouthwashes, having one or more of the compositions of the present invention administered in a suitable liquid carrier.

The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

Compositions for rectal administration may be presented as a suppository with a suitable base comprising, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Compositions may be used as the active ingredient in combination with one or more pharmaceutically acceptable carrier mediums and/or excipients. As used herein, "pharmaceutically acceptable carrier medium" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, the compositions may be combined with pharmaceutically acceptable excipients, and, optionally, sustained-release matrices, such as biodegradable polymers, to form therapeutic compositions. A "pharmaceutically acceptable excipient" includes a non-toxic solid, semi-solid or liquid filler, diluent, encapsulating material or formulation auxiliary of any type.

It will be understood, however, that the total daily usage of the compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; drugs used in combination or coincidential with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Preferred unit dosage formulations are those containing a daily dose or unit, daily sub-dose, or an appropriate fraction thereof, of the administered ingredient. For example, approximately 1-5 mg per day of a compound disclosed herein can reduce the volume of a solid tumor in mice.

The dosage will depend on host factors such as weight, age, surface area, metabolism, tissue distribution, absorption rate and excretion rate. In one embodiment, approximately 0.5 to 7 grams per day of a compound disclosed herein may be administered to humans. Optionally, approximately 1 to 4 grams per day of the compound can be administered to humans. In certain embodiments 0.001-5 mg/day is administered to a human. The therapeutically effective dose level will depend on many factors as noted above. In addition, it is well within the skill of the art to start doses of the composition at relatively low levels, and increase the dosage until the desired effect is achieved.

Compositions comprising a compound disclosed herein may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide coglycolide (co-polymers of lactic acid and glycolic acid).

The compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The compounds may be formulated as aerosols for application, such as by inhalation. These formulations for administration to the respiratory tract can be in the form of an aerosol or solution for a nebulizer, or as a microtine powder for insufflation, alone or in combination with an inert carrier such as lactose. In such a case, the particles of the formulation will, in one embodiment, have diameters of less than 50 microns, in one embodiment less than 10 microns.

Compositions comprising the compounds disclosed herein may be used in combination with other compositions and/or procedures for the treatment of the conditions described above. For example, a tumor may be treated conventionally with surgery, radiation, or chemotherapy combined with one or more compositions of the present invention and then one or more compositions of the present invention may be subsequently administered to the patient to extend the dormancy of micrometastases and to stabilize, inhibit, or reduce the growth of any residual primary tumor.
Additional Embodiments The pharmaceutical compositions of the subject invention can be formulated according to known methods for preparing pharmaceutically useful compositions. Formulations are described in a number of sources which are well known and readily available to those skilled in the art. For example, *Remington's Pharmaceutical Sciences* (Martin EW [1995] Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The methods of the present invention, for example, for inhibiting the growth of a cancerous cell, can be advantageously combined with at least one additional therapeutic method, including but not limited to chemotherapy, radiation therapy, therapy that selectively inhibits Ras oncogenic signaling, or any other therapy known to those of skill in the art of the treatment and management of cancer, such as administration of an anti-cancer agent.

Administration of API-2 (triciribine) as a salt may be carried out. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a subject, such as a human or veterinary patient, in a variety of forms adapted to the chosen route of administration, i.e., orally or parenterally, by intravenous, intramuscular, topical or subcutaneous routes.

Thus, the compounds of the present invention may be systemically administered, e.g., orally, in combination with a pharmaceutically acceptable vehicle (i.e., carrier) such as an inert diluent or an assimilable edible carrier. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of the active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compounds of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds of the invention may be incorporated into sustained-release preparations and devices.

The active agent (i.e., API-2 or pharmaceutically acceptable salts thereof) may also be administered intravenously or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds of the invention may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

In one non-limiting embodiment, the concentration of the active agent in a liquid composition, such as a lotion, can be from about 0.1-25 wt.-%, or from about 0.5-10 wt.-%. In one embodiment, the concentration in a semi-solid or solid composition such as a gel or a powder can be about 0.1-5 wt.-%, preferably about 0.5-2.5 wt.-%. In one embodiment, single dosages for injection, infusion or ingestion will generally vary between 5-1500 mg, and may be administered, i.e., 1-3 times daily, to yield levels of about 0.1-50 mg/kg, for adults. A non-limiting dosage of the present invention can be between 7.5 to 45 mg per clay, administered orally, with appropriate adjustment for the body weight of an individual.

Accordingly, the present invention includes a pharmaceutical composition comprising API-2, as described herein, or pharmaceutically acceptable salts thereof, in combination with a pharmaceutically acceptable carrier. Pharmaceutical compositions adapted for oral, topical or parenteral administration, comprising an amount of API-2, or a pharmaceutically acceptable salt thereof, constitute a preferred embodiment of the invention. The dose administered to a subject, particularly a human, in the context of the present invention should be sufficient to effect a therapeutic response in the patient over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer cell growth, without unmanageable side effects. Administration of API-2 (or a pharmaceutically acceptable salt thereof) can be continuous or at distinct intervals, as can be determined by a person of ordinary skill in the art.

Mammalian species which benefit from the disclosed methods for the inhibition of cancer cell growth, include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used herein interchangeably and are intended to include such human and non-human mammalian species. Likewise, in vitro methods of the present invention can be earned out on cells of such mammalian species.

Patients in need of treatment using the methods of the present invention can be identified using standard techniques known to those in the medical profession.

The following examples are offered by way of illustration and not by way of limitation.

EXAMPLES

Example 1

Cell Lines and Human Tissue Samples

Human ovarian cancer cell lines and human immortalized ovarian surface epithelial cell (HIOSE) lines were described previously (16). HIOSE cells were grown in 199/MDCB 105 (1:1) medium (Sigma) supplemented with 5% fetal bovine serum. Frozen human primary ovarian tumor and normal ovarian tissues were obtained from the Tissue Procurement Facility at H. Lee Moffitt Cancer Center. MicroRNA array and Northern blot analysis. Total RNA from cell lines and tissue samples was isolated with Trizol reagent (Invitrogen, Carlsbad, Calif.). Oligonucleotide arrays were printed with tri-mer oligonucleotide probes (antisense to miRNAs) specific for 515 human and mouse miRNAs on GeneScreen Plus (NEN) membranes, and miRNA expression profiling was performed and analyzed as previously described (7). To ensure accuracy of the hybridIzations, each labeled RNA sample was hybridized with three separate membranes. For Northern blot analysis, 20 ~g of RNA were separated on 15% denaturing polyacrylamide gel and then electroblotted onto a Zeta-Probe GT Blotting Membrane (BioRad). Following transfer, the membrane was dried and UV-crosslinked. The probes were prepared using the Starfire Oligonucleotide Labeling System (Integrated DNA Technologies) according to the manufacturer's protocol. The blots were hybridized overnight at 50° C. in a buffer containing 5×SSC, 20 mM Na2HP04 (pH 7.2), 7% SDS, lx Denhardt's, 0.2 mg/ml salmon sperm DNA, and then washed with IX SSC/1% SDS buffer at 50° C. (13). The probe sequences are:

```
hsa-miR-199a*
5'-AACCAATGTGCAGACTACTGTA-3';    (SEQ ID NO: 1)

hsa-miR-214
5'-CTGCCTGTC TGTGCCTGCTGT-3';    (SEQ ID NO: 2)

hsa-miR-100
5'-CACAAGTTCGGATCTACGGGTT-3'     (SEQ ID NO: 3)
and hsa-miR-200a
5'-ACATCGTTACCAGACAGTGTTA-3'.    (SEQ ID NO: 4)
```

RNase Protection Assay and Quantitative RT-PCR (qRT-PCR).

Expression of miRNAs was also analyzed by RNase protection or mirVana qRT-PCR miRNA detection assay. For RNase protection assay, enriched small RNA was purified using the miRVana miRNA Isolation Kit (Ambion). The mirVana™ miRNA probe construction kit (Ambion) was used to synthesize the 32P-Iabeled miR-214 probe. Probe hybridization and RNase protection were then carried out using the mirVana™ miRNA detection kit (Ambion) according to manufacturer's instructions. After hybridization and RNase treatment, the double-strand products were resolved in a 15% polyacrylamide 8 M urea denaturing gel and visualized using phospho imaging and autoradiography. mirVanaqRT-PCR was performed according to the manufacturer's protocol (Ambion). PCR products were analyzed by electrophoresis on a 7.5% polyacrylamide gel in 0.5× TBE and visualized by ethidium bromide staining.

Antisense Inhibition of miRNA Expression.

2'-O-methyl (2'-O-me) oligoribonucleotides were synthesized by Integrated DNA Technologies. The sequences of 2'-O-methyl-anti-miR-214 and -miR-199a* are: 5'. CUGC-CUGUCUGUGCCUGCUGU-3' (SEQ ID NO: 5) and 5'-AACCAAUGUGCAGACUACUGUA-3' (SEQ ID NO: 6). 2'-O-me-scrambled miR (5'-AAAACCUUUUGAC-CGAGCGUGUU-3') (SEQ ID NO: 7) was used as a control. Cells were grown in 6-well plate (1.7×106 cells/well) for 24 hand transfected with 150 pMol of 2'-O-me oligoribonucleotides per well using Lipofectamine 2000. RNA and protein were extracted after 72 h transfection.

Cloning and Expression of miRNAs.

Expression plasmids of miR-214 and -199a* were created by PCR amplification using human genomic DNA as a template. The primers are

```
miR-214 sense
                                  (SEQ ID NO: 8)
5'-CACCTTTCTCCCTTTCCCCTTACTCTCC-3'
and antisense
                                  (SEQ ID NO: 9)
5'-TTTCATAGGCACCACTCACTTTAC-3',
and miR-199a* sense
                                  (SEQ ID NO: 10)
5'-CACCGCCCAGAAGCCACGA TCCCAAACC-3'
and antisense:
                                  (SEQ ID NO: 11)
5'-TGCCTTTCCCCAGTGCCTCTTCTC-3'.
```

The PCR products (pre-miRNAs) were cloned into pcDNA3.1N5-His-TOPO expression vector (Invitrogen) and confirmed by DNA sequencing. The expression of miRNA was carried out by transfection of the plasmid into the cells using Lipofectamine 2000.

Target In Vitro Reporter Assay.

For luciferase reporter experiments, the 3' UTR segments of PTEN predicted to interact with miR-214 were amplified by PCR from human genomic DNA and inserted into the Mlu I and Hind III sites of pGL3 vector immediately downstream from the stop codon of luciferase (Promega). A2780CP and HIOSE-80 cells were co-transfected in 12-well plates with 0.4 J.lg of the firefly luciferase report vector and 0.08 J.lg of the control vector containing Renilla luciferase, pRL-TK (Promega) as well as with or without 0.5 J.lg of Topo-miR-214. Firefly and Renilla luciferase activities were measured consecutively using dual-luciferase assays (16).

Cell Viability' and Apoptosis Assays.

Cell viability was examined with MTI assay as previously described (21). Apoptosis was detected with annexin V and caspase-3/7 activity (19) (21). For detection of caspase-3/7 activity, cells were cultured in 96-well plates and treated with the agents indicated in the figure legends and analyzed using Caspase-Go 3/7 Assay kit (Promega) according to the manufacturer's instructions.

Results

Frequent deregulation of miR-199a*, -214, -200a and -100 in human ovarian cancer. miRNA profiles have been reported in different types of tumors derived from different organs (3-12), including ovarIan cancer (5). However, toe frequency and pathobiological significance of aberrant miRNA expression in human ovarian cancer have not been well documented. We initially analyzed miRNA expression in 10 human ovarian epithelial tumors and 10 normal human ovarian epithelial cell pools by hybridization of the array containing 515 miRNAs. After normalization of control oligos, the differential expression of miRNAs between ovarian tumors and normal ovarian surface epithelial cells was quantified using a Phosphorimager. Thirty-six of the 515 miRNAs showed differential expression with P values derived from the nonparametric Wilcoxon/Kruskal-Wallis test being <0.05. Of them, 14 miRNAs that changed more than 1 fold were confirmed by Northern and/or qRT-PCR analysis (FIGS. 1A, IB and data not shown). To further validate our results, miR-199a*, miR-214, miR-200a and miR-100, 4 of the most differentially expressed miRNAs, were analyzed in 30 primary ovarian cancers (Table 1). As compared to normal ovarian cells, more than half of the primary tumors exhibited elevated levels of miR-199a* (53%, 16/30) and miR-214 (56%; 17/30) and downregulated miR-100 (76%, 23/30). Moreover, increased miR-200a was detected in 43% of primary ovarian carcinomas examined (Table 1). Further, while the number of specimens is relatively small, the deregulation of these four miRNAs seems to be associated with high grade and late stage tumors (Table 2). These data suggest that alterations of miR-199a*, miR-214, miR-200a and miR-100 are recurrent event and could be involved in ovarian cancer progression.

The miR-214 Targets PTEN Leading to Activation of the Akt Pathway.

Since miR-214 was one of the most frequently up-regulated miRNAs in the ovarian tumors (Table 2 and FIG. 1) and has recently been shown to play an important role in Zebrafish muscle development (22), we next examined its potential targets by searching the database. Among the candidates targeted, 3'UTR Qf human PTEN contains a putative region (nucleotides 3257-3264, NM_000314) (SEQ ID NO: 12) that matches to the seed sequence ofhsa-miR-214, which is also conserved in mouse (SEQ ID NO: 13) and rat (SEQ ID NO: 14) (FIG. 2A). To examine whether PTEN is indeed the target of miR-214, a miR-214-negative cell line HIOSE-80 (FIGS. 2B and 3A) was transfected with pcDNA3.1N5-His-Topo-miR-214. The cells transfected with pcDNA3.1V5-His-Topo vector alone and pcDNA3.1N5-His-Topo-miR-199a* were used as controls Immunoblotting and RT-PCR analyses revealed that PTEN protein but not mRNA was considerably decreased in miR-214-transfected HIOSE-80 cells (FIG. 2B). In contrast, knockdown of miR-214 by 2'-O-methyl miR-214 in A2780CP cells, which express high levels of endogenous miR-214 (FIG. 3A), increased the protein level of PTEN (FIGS. 2C and 2D). Further, the phosphorylation levels of Akt, a major target of PTEN (20), and Akt substrates GSK3J3 and p70S6K were elevated by ectopic expression of miR-214 (FIG. 2B) and decreased by knockdown of miR-214 (FIG. 2C), suggesting that miR-214 targets the PTEN/Akt pathway. To further demonstrate that PTEN is negatively regulated by miR-214, we constructed luciferase reporters with wild-type (pGL3-PTEN-3'UTR) and mutated (pGL3-PTENmut-3'UTR) 3'UTR of PTEN (SEQ ID NO: 15) (FIG. 2A). Both the wild-type and the mutant reporters were introduced into A2780CP (miR-214-positive) and HIOSE-80 (miR-214– negative) cells, respectively. Luciferase activity of the wild-type, but not mutant, PTEN-3'UTR reporter was significantly suppressed in miR-214-positive A2780CP cells but not in miR-214-negative HOSE-80 cells. Moreover, ectopic expression of miR-214 in HlOSE-80 cells inhibited the wild-type but not the mutated reporter activity (FIG. 2E). Having observed that miR-214 negatively regulates PTEN in cell culture system, we asked if this regulation is seen in vivo. PTEN protein was examined in a same series of normal ovary and primary ovarian tumor specimens for expression of miRNAs (FIG. 2F). Of the 30 primary ovarian tumors, 13 had downregulation of PTEN and 17 had overexpression of miR-214 (Table 2). Of the 17 tumors with elevated miR-214, 11 (65%) also had decreased PTEN levels (P<0.0001). These data further support the findings that the PTEN is a direct target of miR-214.

miR-214 is an Anti-Apoptotic Factor that is Associated with Cisplatin Resistance.

Figure 3D:
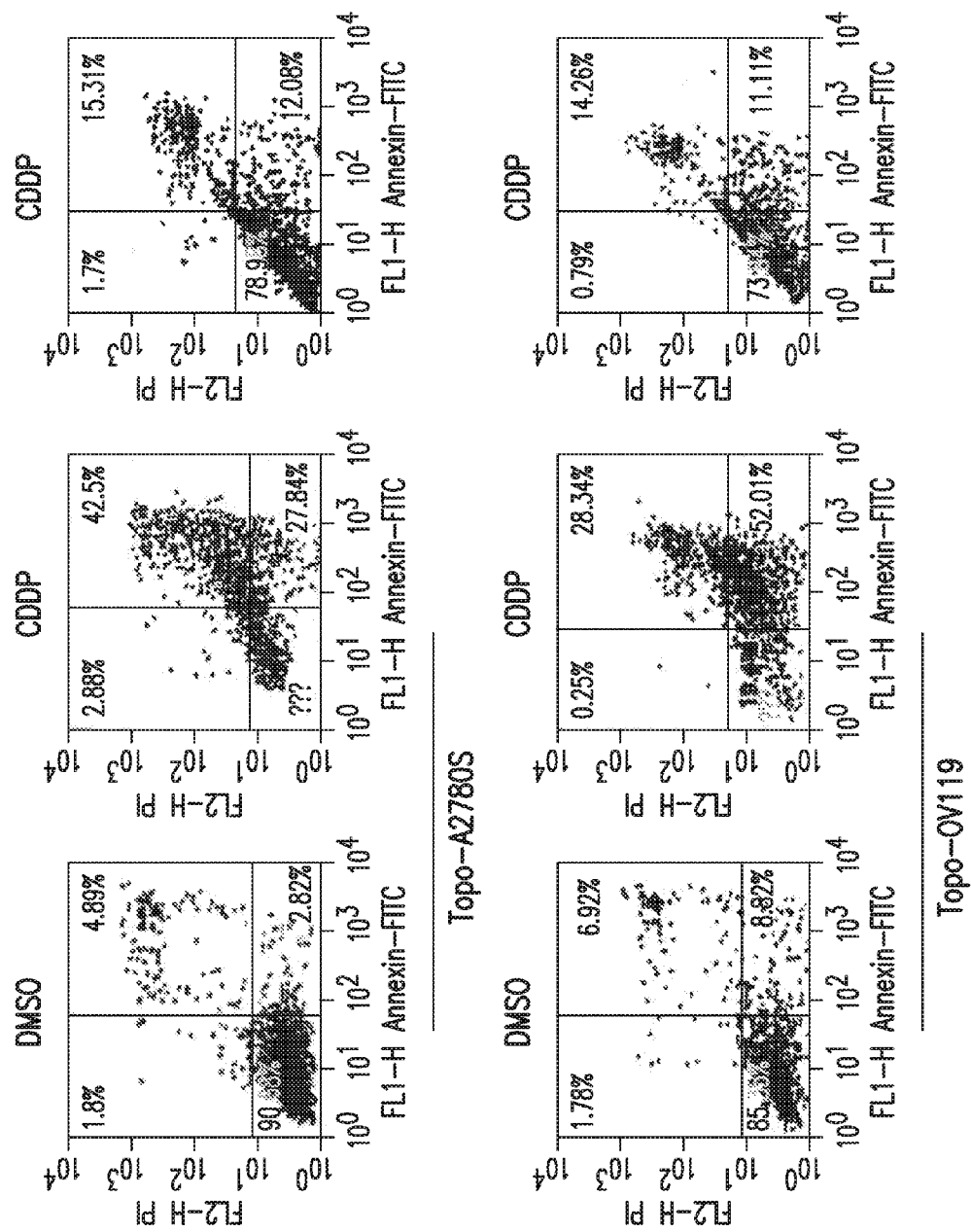
Figure 4B:
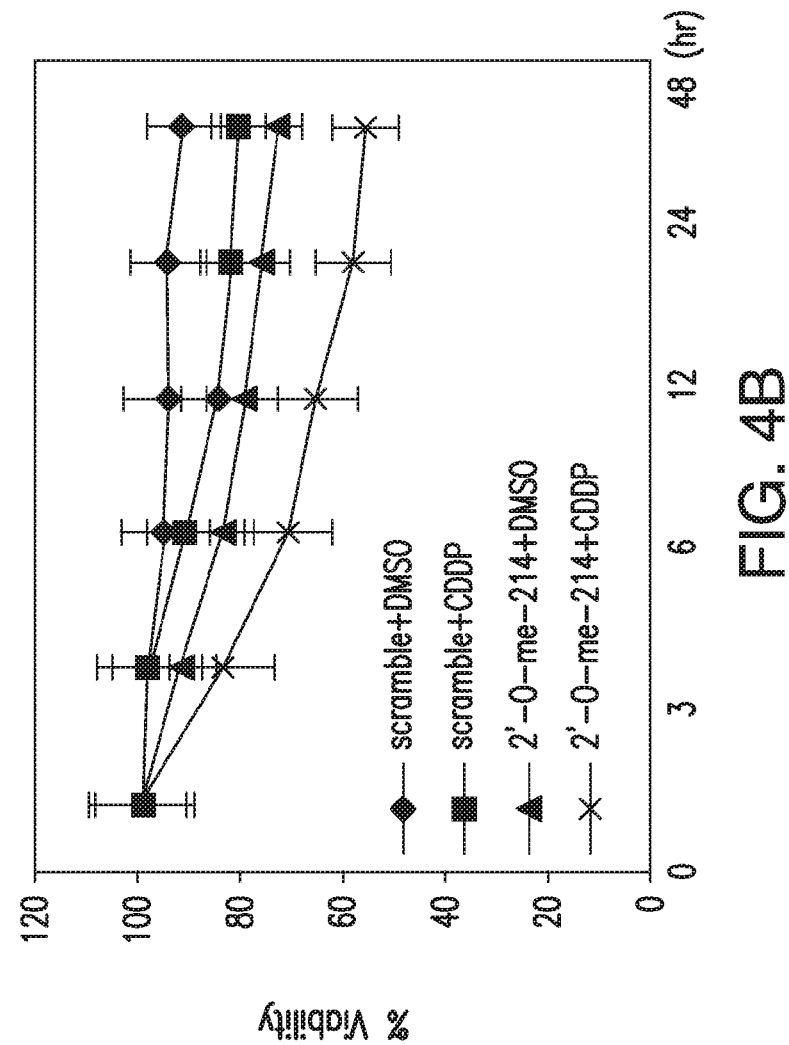
FIG. 4A-FIG. 4C Knockdown of miR-214 sensitizes A2780CP cells to cisplatin. (A) A2780CP, a cisplatin-resistant cell line and expressing elevated levels of endogenous miR-214, was transfected with 2'-O-me-anti-miR-214 or scramble 2'-O-me oligonucleotides and assayed with qRT-PCR with primers of miR-214 (top) and U6 (bottom). (B) MTT assay. The 2'-O-me-anti-miR-214- or scramble 2'-O-me-transfected A2780CP cells were treated with 20 uM of cisplatin or DMSO vehicle for the indicated times and examined for cell viability. (C) Flow cytometry. Indicated cells were treated with cisplatin or DMSO for 12 h and the subG1 population was identified by flow cytometry.
Figure 4A:
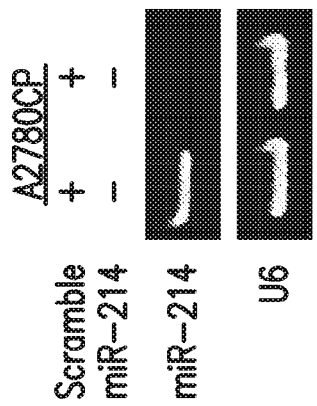
Figure 4C:
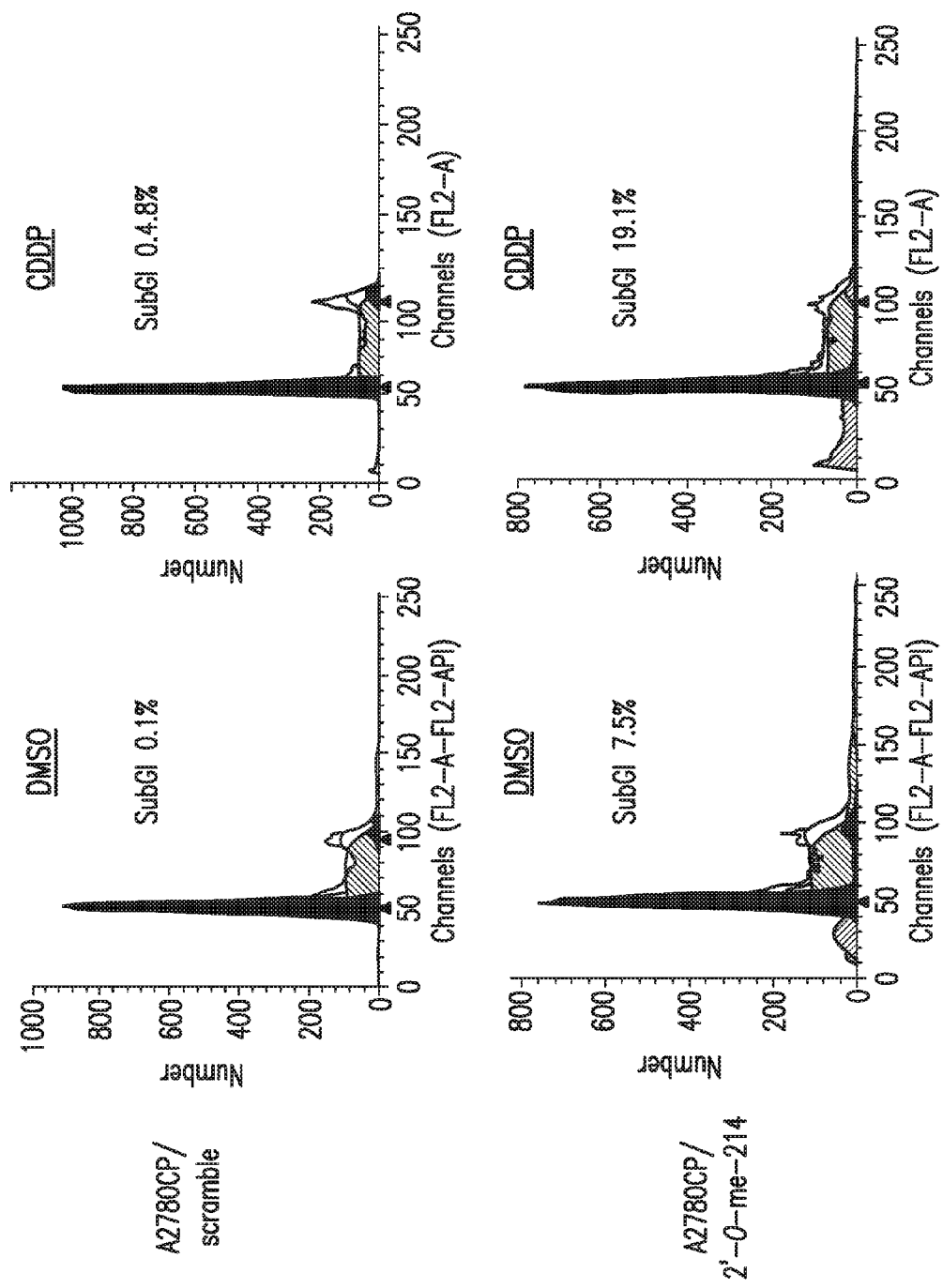

Since Akt is a major cell survival pathway and its activation plays a key role in multiple drug resistance including cisplatin (20), we next examined the effects of miR-214 on cell survival and cisplatin resistance. FIG. 3A shows that expression levels of miR-214 are low in immortalized human surface epithelial cell lines, HlOSE-80 and MCC-3 as well as A2780S and OV119 cells as compared to other ovarian cancer cell lines examined Since A2780S and OV119 cells are sensitive to cisplatin (17), we ectopically expressed miR-214 in these 2 cell lines and examined if expression of miR-214 renders the cells resistant to cisplatin-induced cell death. Following the transfection of pcDNA3.1N5-His-Topo-miR-214 and 0418 selection, stable pool cells were obtained and the expression of miR-214 was confirmed by qRT-PCR (FIG. 3B). The cells transfected with miR-214 and pcDNA3.1N5-His-Topo vector were treated with cisplatin or vehicle DMSO. As shown in FIGS. 3C and 3D, the expression of miR-214 confers the cells resistant to cisplatin-induced cell death, suggesting that miR-214 is an anti-apoptotic factor. Having observed an elevated level of miR-214 in cisplatin-resistant A2780CP cells (FIG. 3A), we next examined if knockdown of miR-214 is able to override cisplatin resistance. A2780CP cells were transfected with 2'-O-methyl-anti-miR-214. The cells transfected with 2'-O-methyl-scramble-miR were used as control. Following 72 h transfection, qRT-PCR analysis showed that level of miR-214 was significantly decreased in the cells treated with 2'-O-methyl-anti-miR-214 (FIG. 4A). Further, the cells were treated with cisplatin or vehicle DMSO. Cell viability analysis revealed that knockdown of miR-214 alone reduced cell survival about 20% in A2780CP cells. Moreover, blocking miR-214 expression considerably sensitized A2780CP cells to cisplatin-induced apoptosis (FIGS. 4B and 4C). Taken collectively, these data indicate that miR-214 could play an important role in cisplatin resistance.

Akt Inhibitor, API-2/Triciribine/TCN, or Introduction of PTEN cDNA Lacking 3'-UTR Reduces miR-214-Induced Cell Survival and CDDP Resistance.

Figure 5A:
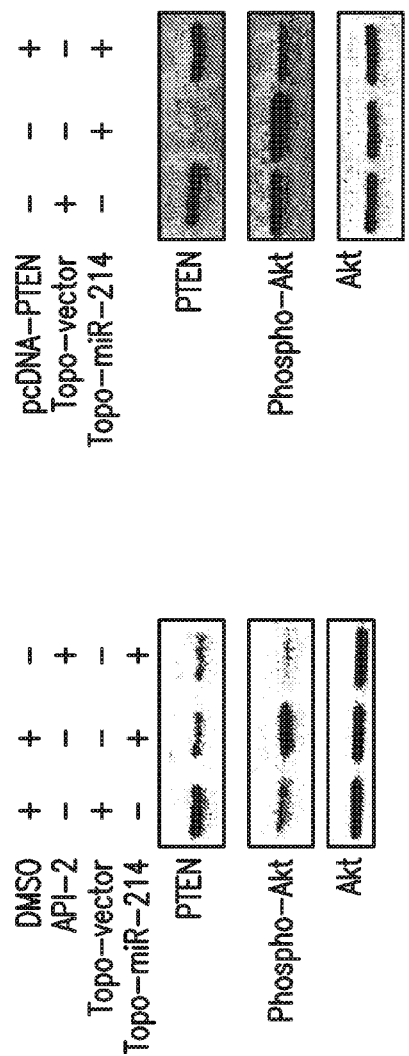
FIG. 5A-FIG. 5B Inhibition of Akt or transfection of PTEN-cDNA lacking 3'UTR overrides miR-214-induced cell survival. (A) Topo-miR-214 and vector stably transfected A2780S cells were treated with Akt inhibitor API-2/TCN (10 uM) and/or cisplatin (20 uM). The cells treated with DMSO were used as control. After 24 h of tOO=treatment, cells were subjected to immunoblotting analysis with indicated antibodies (upper) and assayed for caspase 3/7 activity (bottom). (B) A2780S cells were stably transfected with indicated plasmids and assayed for expression of PTEN, phospho-Akt-S473 and total Akt (upper). After treatment with or without cisplatin for 24 h, cells were examined for caspase 3/7 activity (bottom).
Figure 5B:
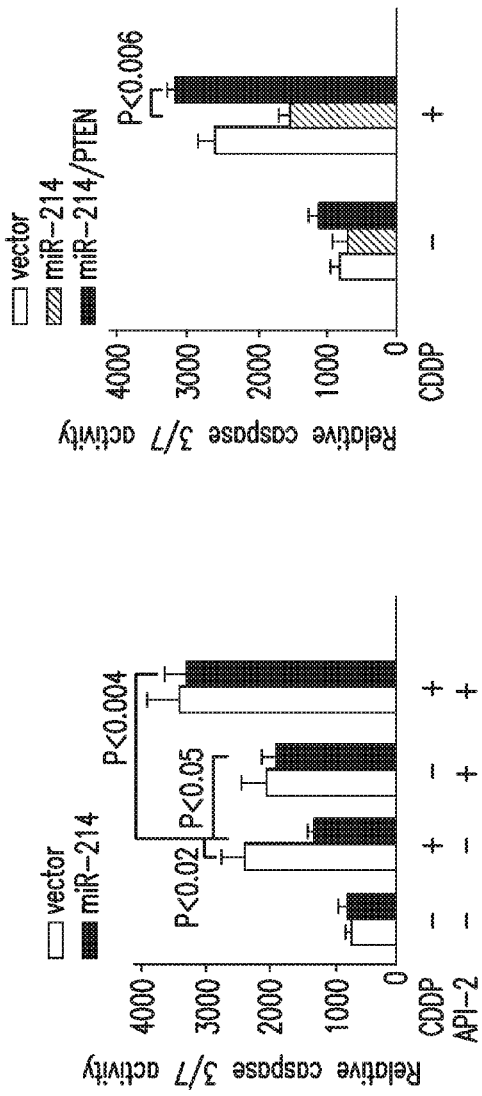

Since ectopic expression of miR-214 reduces PTEN expression leading to activation of Akt pathway (FIGS. 2B and 2C) and inhibition of the cisplatin-induced cell death (FIGS. 3C and 3D), we next reasoned that inhibition of Akt should override miR-214-induced cell survival and cisplatin resistance. We have previously identified a specific Akt inhibitor, API-2/TCN, which is currently in clinic trail (20, 21). To test this hypothesis, miR-214-transfected A2780S cells were treated with API-2/TCN, in combination with or without cisplatin. The cells transfected with Topo-vector were used as control. As shown in FIG. 5A, API-2 abrogated miR-214-activated Akt and significantly inhibited miR-214-induced cell survival and cisplatin resistance. It has been documented that miRNAs negatively regulate the expression of their targets primarily through base-pairing interactions in the mRNA 3' UTR, leading to mRNA degradation or translational inhibition which depends on whether it is partially matched or completely matched with the target genes. Since miR-214 downregulates PTEN through binding to 3'UTR of PTEN mRNA (FIG. 2), ectopic expression of PTEN by transfection of the cDNA that only contains the coding region of PTEN should escape the regulation by miR-214, and thus attenuate or decrease miR-214 function. To this end, pcDNA-PTEN lacking 3'UTR was. introduced into miR-214-transfected A2780S cells and then treated with or without cisplatin for 24 h. As shown in FIG. 5B, expression of PTEN decreased Akt activation induced by miR-214 and sensitized the miR-214-A2780S cells to cisplatin-induced apoptosis. These results further indicate that the PTEN/Akt pathway is a major target of miR-214 and largely mediates miR-214 anti-apoptotic function.

Profiles of miRNA have been reported in different types of human malignancy (3-12).

Thus far, there is a global miRNA profiling study of human ovarian cancer in combination with breast cancer and melanoma, which showed frequent co-deregulation of a number of miRNAs in ovarian and breast cancers and melanoma (5). In the present report, we demonstrated that up expression of miR-214, -199a* and -200a and downregulation of miR-100 are recurrent events in ovarian cancer and are associated with late stage and high grade tumors suggesting that deregulation of these four miRNAs could contribute to ~ ovarian tumor progression rather than initiation.

Previous studies have shown that miRNA could serve as "oncogene" or "tumor suppressor gene" and regulate different cellular processes by targeting hundreds of genes. We showed that miR-214 is highly expressed in the cisplatin-resistant A2780CP cell line as compared to its corresponding cisplatin-sensitiv~ cell line A2780S. Knockdown of miR-214 overrides cisplatin resistance in A2780CP cells, whereas ectopic expression of miR-214 renders A2780S and OV119 cells resistant to cisplatin-induced apoptosis. It has been well documented that constitutive activation of Akt contributes to chemoresistance in different types of tumors including ovarian carcinoma (20). miR-214 blocks PTEN translation by binding of its seed sequence to 3'UTR of PTEN mRNA, which leads to activation of the Akt pathway (FIG. 2). Inhibition of Akt using a small molecule inhibitor, API-2, hirgely abrogates miR-214-induced cell survival and cisplatin resistance, suggesting that PTEN is a major target of miR-214.

Mutation of PTEN has been detected only in endometrioid ovarian cancer (23).

However, downregulation of PTEN protein is frequently detected in serous and ucinous epithelial ovarian tumors (24). The mechanism of downregulation of PTEN was thought to be promoter hypermethylation. However, the demethylation agent 5-aza-2' deoxycytidine failed to restore PTEN protein expression, suggesting that PTEN is highly regulated at the translational level and that methylation of the PTEN gene plays a subordinate role in ovarian cancer (25). In the present study, we showed that PTEN is negatively regulated by miR-214 at the protein level and that downregulation of PTEN largely correlates with elevated levels of miR-214 in ovarian cancer (FIG. 2F). Therefore, these data indicate that miR-214 could be a causal factor of the downregulation of PTEN in human ovarian cancer.

In summary, our study suggests that deregulation of miR-214, -199a* -200a and -100 is a frequent event in ovarian cancer, which is associated with tumor progression, and that miR-214 induces cell survival and cisplatin resistance by targeting, the PTEN/Akt pathway.

Therefore, these miRNAs could play an important role in the pathogenesis of this malignancy and are potential targets for ovarian cancer intervention.

This invention has been described with reference to its preferred embodiments. Variations and modifications of the invention, will be obvious to those skilled in the art from the foregoing detailed description of the invention. It is intended that all of these variations and modifications be included within the scope of this invention.

What is claimed is:

1. A method for treating ovarian cancer in a mammal comprising:
   (i) determining whether the tumor or cancer cell overexpresses an Akt kinase, and
   (ii) if the tumor or cancer cell overexpresses Akt kinase, treating the tumor or cancer with an effective amount of 10 mg/m² or less of a compound of the formula:

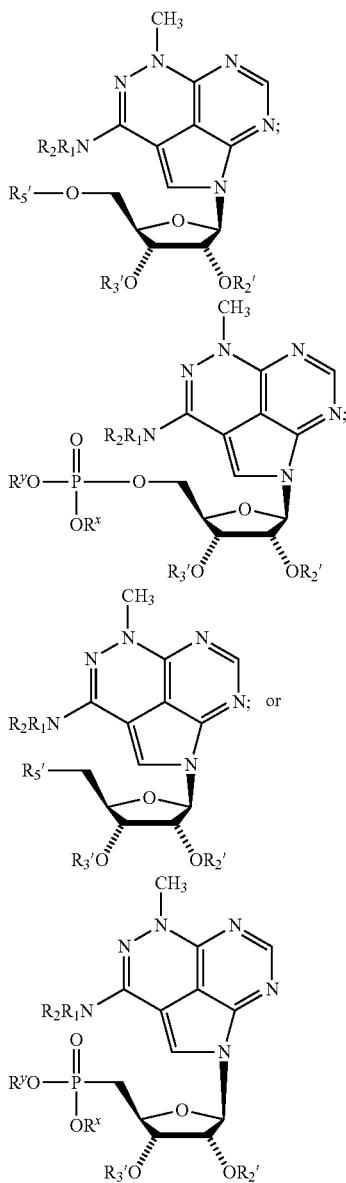

wherein each $R_2'$, $R_3'$ and $R_5'$ are independently hydrogen, optionally substituted phosphate or phosphonate; acyl; alkyl; amide, sulfonate ester including alkyl or arylalkyl; sulfonyl, including methanesulfonyl and benzyl, wherein the phenyl group is optionally substituted with one or more substituents; optionally substituted arylsulfonyl; a lipid, including a phospholipid; an amino acid; a carbohydrate; a peptide; or cholesterol; or other pharmaceutically acceptable leaving group that, in vivo, provides a compound wherein $R_2'$, $R_3'$ or $R_5$ is independently H or mono-, di- or tri-phosphate;

wherein $R^x$ and $R^y$ are independently hydrogen, optionally substituted phosphate; acyl; amide, alkyl; aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group;

wherein $R_1$ and $R_2$ each are independently H, optionally substituted straight chained, branched or cyclic alkyl; alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl.

2. The method of claim 1, wherein the subject has been diagnosed with ovarian cancer.

3. The method of claim 1, wherein the level of Akt kinase expression is determined by assaying the cancer for the presence of a phosphorylated Akt kinase.

4. The method of claim 1, wherein the level of Akt kinase expression is determined by assaying the cancer for the presence of a phosphorylated Akt kinase with an antibody.

5. A method of treating ovarian cancer in a mammal wherein the ovarian cancer overexpresses Akt kinase comprising administering to the mammal an effective amount of 10 mg/m² or less of at least one compound selected from the group consisting of:

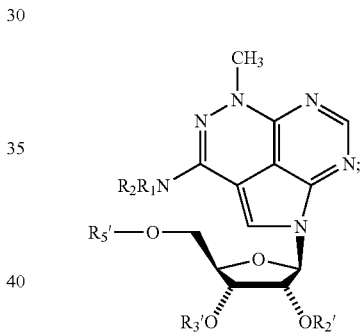

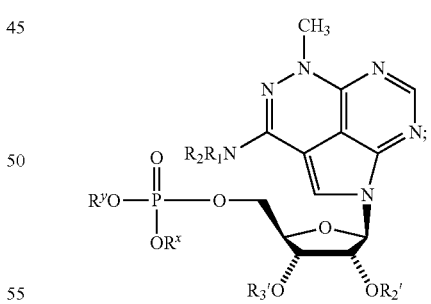

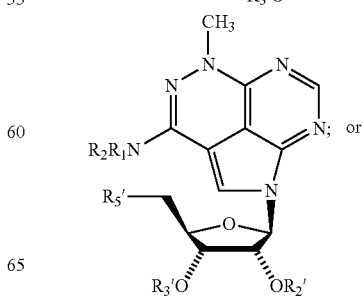

-continued

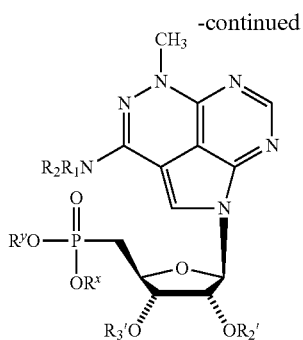

wherein each $R_2'$, $R_3'$ and $R_5'$ are independently hydrogen, optionally substituted phosphate or phosphonate; acyl; alkyl; amide, sulfonate ester including alkyl or arylalkyl; sulfonyl, including methanesulfonyl and benzyl, wherein the phenyl group is optionally substituted with one or more substituents; optionally substituted arylsulfonyl; a lipid, including a phospholipid; an amino acid; a carbohydrate; a peptide; or cholesterol; or other pharmaceutically acceptable leaving group that, in vivo, provides a compound wherein $R_2'$, $R_3'$ or $R_5'$ is independently H or mono-, di- or tri-phosphate;

wherein $R^x$ and $R^y$ are independently hydrogen, optionally substituted phosphate; acyl; amide, alkyl; aromatic, polyoxyalkylene such as polyethyleneglycol, optionally substituted arylsulfonyl; a lipid, including a phospholipid; an amino acid; a carbohydrate; a peptide; or cholesterol; or other pharmaceutically acceptable leaving group;

wherein $R_1$ and $R_2$ each are independently H, optionally substituted straight chained, branched or cyclic alkyl, alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkyl sulfonyl, aryl sulfonyl, aralkyl sulfonyl;

wherein the compound is administered one time per week for three weeks followed by a one week period wherein the compound is not administered.

6. The method of claim 5, wherein the dosing schedule is repeated at least twice.

7. The method of claim 5, wherein the dosing schedule is repeated at least 4 times.

* * * * *

SEQUENCE LISTING

```
<160> NUMBER OF SEQ ID NOS: 15

<210> SEQ ID NO 1
<211> LENGTH: 22
<212> TYPE: DNA
<213> ORGANISM: Artificial
<220> FEATURE:
<223> OTHER INFORMATION: Synthetic probe sequence of hsa-miR-199a

<400> SEQUENCE: 1
aaccaatgtg cagactactg ta                                              22

<210> SEQ ID NO 2
<211> LENGTH: 21
<212> TYPE: DNA
<213> ORGANISM: Artificial
<220> FEATURE:
<223> OTHER INFORMATION: Synthetic probe sequence of hsa-miR-214

<400> SEQUENCE: 2
ctgcctgtct gtgcctgctg t                                               21

<210> SEQ ID NO 3
<211> LENGTH: 22
<212> TYPE: DNA
<213> ORGANISM: Artificial
```

```
<220> FEATURE:
<223> OTHER INFORMATION: Synthetic probe sequence of hsa-miR-100

<400> SEQUENCE: 3
cacaagttcg gatctacggg tt                                           22

<210> SEQ ID NO 4
<211> LENGTH: 22
<212> TYPE: DNA
<213> ORGANISM: Artificial
<220> FEATURE:
<223> OTHER INFORMATION: Synthetic probe sequence of hsa-miR-200a

<400> SEQUENCE: 4
acatcgttac cagacagtgt ta                                           22

<210> SEQ ID NO 5
<211> LENGTH: 21
<212> TYPE: RNA
<213> ORGANISM: Artificial
<220> FEATURE:
<223> OTHER INFORMATION: Synthetic sequence of 2'-O-methyl-anti-miR-214

<400> SEQUENCE: 5
cugccugucu gugccugcug u                                            21

<210> SEQ ID NO 6
<211> LENGTH: 22
<212> TYPE: RNA
<213> ORGANISM: Artificial
<220> FEATURE:
<223> OTHER INFORMATION: Synthetic sequence of 2'-O-methyl-anti-miR-
      199a*

<400> SEQUENCE: 6
aaccaaugug cagacuacug ua                                           22

<210> SEQ ID NO 7
<211> LENGTH: 23
<212> TYPE: RNA
<213> ORGANISM: Artificial
<220> FEATURE:
<223> OTHER INFORMATION: Synthetic sequence of 2'-O-me-scrambled miR

<400> SEQUENCE: 7
aaaaccuuuu gaccgagcgu guu                                          23

<210> SEQ ID NO 8
<211> LENGTH: 28
<212> TYPE: DNA
<213> ORGANISM: Artificial
<220> FEATURE:
<223> OTHER INFORMATION: Synthetic primer of miR-214 sense

<400> SEQUENCE: 8
cacctttctc cctttcccct tactctcc                                     28

<210> SEQ ID NO 9
<211> LENGTH: 24
<212> TYPE: DNA
<213> ORGANISM: Artificial
<220> FEATURE:
<223> OTHER INFORMATION: Synthetic primer of miR-214 anti-sense

<400> SEQUENCE: 9
tttcataggc accactcact ttac                                         24
```

```
<210> SEQ ID NO 10
<211> LENGTH: 28
<212> TYPE: DNA
<213> ORGANISM: Artificial
<220> FEATURE:
<223> OTHER INFORMATION: Synthetic primer of miR-199a* sense

<400> SEQUENCE: 10
caccgcccag aagccacgat cccaaacc                                      28

<210> SEQ ID NO 11
<211> LENGTH: 24
<212> TYPE: DNA
<213> ORGANISM: Artificial
<220> FEATURE:
<223> OTHER INFORMATION: Synthetic primer of miR-199a* antisense

<400> SEQUENCE: 11
tgcctttccc cagtgcctct tctc                                          24

<210> SEQ ID NO 12
<211> LENGTH: 35
<212> TYPE: DNA
<213> ORGANISM: Artificial
<220> FEATURE:
<223> OTHER INFORMATION: Synthetic sequence of H. sapiens PTEN 3-UTR

<400> SEQUENCE: 12
ttattttact agttttcaat cataatacct gctgt                              35

<210> SEQ ID NO 13
<211> LENGTH: 35
<212> TYPE: DNA
<213> ORGANISM: Artificial
<220> FEATURE:
<223> OTHER INFORMATION: Synthetic sequence of M. Musculus PTEN 3-UTR

<400> SEQUENCE: 13
ttatttttat taattttcaa tcatatacct actgt                              35

<210> SEQ ID NO 14
<211> LENGTH: 35
<212> TYPE: DNA
<213> ORGANISM: Artificial
<220> FEATURE:
<223> OTHER INFORMATION: Synthetic sequence of R. Norvericus PTEN 3-UTR

<400> SEQUENCE: 14
ttatttttat taattttcaa tcatatacct actgt                              35

<210> SEQ ID NO 15
<211> LENGTH: 21
<212> TYPE: DNA
<213> ORGANISM: Artificial
<220> FEATURE:
<223> OTHER INFORMATION: Synthetic pGL3-PTENmut-UTR

<400> SEQUENCE: 15
ttcaatcata atacctgaca t                                             21
```